United States Patent [19]

Pascal et al.

[11] Patent Number: 5,514,800
[45] Date of Patent: *May 7, 1996

[54] SUBSTITUTED IMIDAZOLYL-ALKYL-PIPERAZINE AND -DIAZEPINE DERIVATIVES

[75] Inventors: Jean C. Pascal, Cachan, France; Chi-Ho Lee, Palo Alto, Calif.; Brian J. Alps, Linlithgow, Scotland; Henri Pinhas, Paris, France; Roger L. Whiting, Los Altos, Calif.; Calum B. MacFarlane, Linlithgow, Scotland; Serge Beranger, Bretigny-Sur-Cedres, France

[73] Assignee: Syntex Pharmaceuticals, Ltd., Maidenhead, England

[ * ] Notice: The term of this patent shall not extend beyond the expiration date of Pat. No. 5,091,428.

[21] Appl. No.: 124,518

[22] Filed: Sep. 20, 1993

Related U.S. Application Data

[62] Division of Ser. No. 688,193, Apr. 19, 1991, Pat. No. 5,276,034, which is a division of Ser. No. 260,969, Oct. 21, 1988, Pat. No. 5,043,447, which is a continuation-in-part of Ser. No. 42,181, Apr. 24, 1987, Pat. No. 4,829,065.

[51] Int. Cl.⁶ .................. C07D 403/06; C07D 243/08
[52] U.S. Cl. ............................. 544/370; 540/575
[58] Field of Search ................ 544/370; 514/252; 540/575

[56] References Cited

U.S. PATENT DOCUMENTS

| | | | |
|---|---|---|---|
| 3,362,956 | 1/1968 | Archer | 514/253 |
| 3,491,098 | 1/1970 | Archer | 514/252 |
| 4,829,065 | 5/1989 | Pascal | 514/255 |
| 5,010,075 | 4/1991 | Pascal et al. | 514/218 |
| 5,091,428 | 2/1992 | Pascal et al. | 514/252 |

*Primary Examiner*—Cecilia Tsang
*Attorney, Agent, or Firm*—Heller Ehrman White & McAuliffe

[57] ABSTRACT

Substituted imidazolyl-alkyl-piperazine and diazepine derivatives of Formula A:

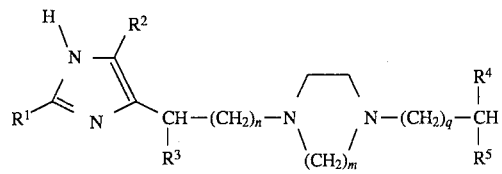

wherein $R^1$, $R^2$, $R^3$, $R^4$, $R^5$, m, n and q are defined as in the specification, and the pharmaceutically acceptable salts thereof. The compounds have calcium entry blocking activity with selectivity for cerebral blood vessels, and have protective activity against some of the deleterious effects resultant upon cerebral ischemia.

10 Claims, No Drawings

SUBSTITUTED IMIDAZOLYL-ALKYL-PIPERAZINE AND -DIAZEPINE DERIVATIVES

CROSS-REFERENCE TO RELATED APPLICATIONS

This application is a division of application Ser. No. 07/688,193, filed Apr. 19, 1991, now U.S. Pat. No. 5,276,034, incorporated by reference; which in turn is a division of application Ser. No. 07/260,969, filed Oct. 21, 1988, now U.S. Pat. No. 5,043,447, incorporated by reference; which in turn is a continuation-in-part of U.S. Ser. No. 042,181, filed Apr. 24, 1987, now U.S. Pat. No. 4,829,065, incorporated herein by reference, and claims priority from EPO application Ser. No. 88.303646.9, filed Apr. 22, 1988, also incorporated herein by reference.

This application is also related to U.S. Ser. No. 260,628, now U.S. Pat. No. 4,973,591, and its division, Ser. No. 585,436, now U.S. Pat. No. 5,063,220, both incorporated herein by reference, wherein preferred parenteral formulations, most preferably with 1-(diphenylmethyl)-4-[(2-(4-methylphenyl)-5-methyl-1 H-imidazol-4-yl)methyl]piperazine, tartrate are disclosed.

This application is also related to U.S. Ser. No. 260,965, now U.S. Pat. No. 5,142,052, incorporated herein by reference, wherein related synthetic processes are disclosed.

BACKGROUND OF THE INVENTION

1. Field of the Invention

This invention relates to substituted imidazolyl-alkyl-piperazine and diazepine derivatives, the pharmaceutically acceptable salts thereof, methods of making these compounds, and pharmaceutical compositions containing these compounds. The compounds of this invention have calcium entry blocking activity with selectivity for cerebral blood vessels, and have protective activity against some of the deleterious effects resultant upon cerebral ischemia.

The compounds of this invention are useful for treating mammals having any of a variety of disease states, including:

diseases treated by direct neuronal protection, such as ischemia including focal and global ischemia, spinal injuries, head trauma, and neurological diseases such as Alzheimer's and Huntington's chorea;

diseases treated by inhibition of sodium ion, such as uraemic and hyponatraemic encephalopathy; and diseases treated with calcium channel antagonists, including:

diseases treated by inhibiting cerebrovascular vasospasm and by cerebrovascular vasodilation, such as migraine, stroke, vasospasm due to subarachnoid hemorrhage, epilepsy or epileptic psychotic symptoms, and cerebrovascular ischemia induced by cocaine abuse; and cardiovascular diseases, such as hypertension, angina, stable and unstable angina, Prinzmetal angina, arrhythmia, thrombosis, embolism, and congestive heart failure such as chronic or acute cardiac failure; and ischemia of lower legs due to peripheral vascular disease, e.g., intermittent claudication;

spasms of smooth muscle: such as the ureter, the bladder, uterine cramps, diuresis, and irritable bowel syndrome; and uses during surgery: such as bypass grafts, angiography, angioplasty, organ preservation during transplant, hypertensive crisis, or post operative hypertension.

2. Background Information and Related Art

Substituted piperazines have been described as having a variety of pharmaceutical activities.

For example, U.S. Pat. No. 3,362,956 and its CIP 3,491,098, disclose a series of substituted piperazines to be useful as tranquilizers, sedatives, adrenolytic agents, hypothermic agents, anti-convulsants, hypotensive agents and cardiovascular agents. For example, in the '956 patent, compounds of the formula:

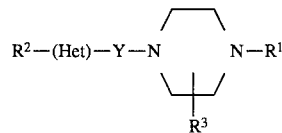

wherein $R^1$ is a lower-alkyl, hydroxy-lower alkyl, phenyl or substituted-phenyl, phenyl-lower-alkyl, or substituted-phenyl-lower-alkyl, benzhydryl or substituted benzhydryl, phenyl-lower-alkenyl or substituted-phenyl- lower-alkenyl, or pyridyl radical; $R^2$ is hydrogen or from one to two lower-alkyl radicals; Y is lower-alkylene of from one to six carbon atoms; and Het is a heterocyclic radical selected from the group consisting of bicyclic aromatic nitrogen heterocyclic radicals having fused five and six membered rings and containing from two to three ring nitrogen atoms which can be in any position of the two rings, for example, radicals derived from indazole (e.g. 2-azaindole, 4-azaindole, 5-azaindole, 6-azaindole, 7-azaindole), pyrrolo[2,3-d]-pyrimidine, benzimidazole and pyrido[2,1-c]-s-triazole; a benz[g]-3-indolyl radical; a 4(5)-imidazolyl radical; a 3-thianaphthenyl radical; a 3-quinolyl radical; a 3,4-dihydro-1-isoquinolyl radical; or 1,2,3,4-tetrahydro-1-isoquinolyl radical or such heterocyclic radicals substituted in any available position by from one to three substituents, defined hereinafter as $R^2$, for example methyl ethyl propyl and isobutyl; lower-alkoxy, for example, methoxy, ethoxy, propoxy, and butoxy; halogen, including fluorine, chlorine, bromine, and iodine; lower-alkylmercapto, for example, methylmercapto, ethylmercapto, propylmercapto, and isobutylmercapto; lower-alkylsulfinyl, for example, methylsulfinyl, ethylsulfinyl, propylsulfinyl, and isobutylsulfinyl; lower-alkylsulfonyl, for example, methylsulfonyl, ethylsulfonyl, propylsulfonyl, isopropylsulfonyl; trifluoromethyl; hydroxy; methylenedioxy; or ethylenedioxy, wherein the lower-alkyl moiety of the said substituents contain from one to four carbon atoms; are disclosed.

In the '098 patent compounds of the formula:

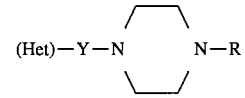

wherein R is hydrogen or a lower-alkyl, hydroxy-lower-alkyl, phenyl, phenyl-lower-alkyl, benzhydryl, phenyl-lower-alkenyl, cycloalkyl-lower- alkyl, or pyridyl radical; Y is lower-alkylene of from one to six carbon atoms; and Het is a 4(5)-imidazolyl radical; are disclosed.

None of the prior art teaches 4(5)-imdazolyl-substituted piperazine or diazepine derivatives substituted or useful in the manner of this invention. Compounds having the range of activity, such as those of the present invention, have remained desired.

SUMMARY OF THE INVENTION

A first aspect of this invention encompasses compounds having the structures represented by Formula A:

$$\underset{R^1}{\overset{H}{\underset{\diagdown}{N}}}\underset{N}{\overset{R^2}{=}}\underset{\underset{R^3}{|}}{CH}-(CH_2)_n-N\underset{(CH_2)_m}{\diagdown}N-(CH_2)_q-\underset{\underset{R^5}{|}}{\overset{R^4}{|}}{CH} \quad \text{FORMULA A}$$

wherein:
$R^1$ is aryl, lower alkyl, cycloalkyl or hydrogen;
$R^2$ is aryl, lower alkyl or hydrogen;
$R^3$ is lower alkyl, hydroxy, or hydrogen;
$R^4$ is aryl or hydrogen;
$R^5$ is aryl or hydrogen;
m is two or three;
n is zero, one or two,
provided that when $R^3$ is hydroxy, n is one or two; and
q is zero, one, two, or three;
and the pharmaceutically acceptable salts thereof.

A further aspect of the present invention encompasses methods of making compounds of Formula A wherein $R^3$ is lower alkyl or hydrogen and n is zero, by reacting a substituted amidine of the formula:

$$\underset{R^1}{\overset{H_2N\diagdown\,\diagup NH.HCl}{\underset{|}{C}}}$$

with a substituted dione of the formula:

$$H(CH_2)_a-CH_2-\overset{\overset{O}{\|}}{C}-\overset{\overset{O}{\|}}{C}-R^2$$

wherein a is an integer from zero to four; and a substituted-4-piperazine or a substituted-4-diazepine of the formula:

$$H-N\underset{(CH_2)_m}{\diagdown}N-(CH_2)_q-\underset{\underset{R^5}{|}}{\overset{R^4}{|}}{CH}$$

in the presence of a lithium reagent.

A still further aspect of the present invention encompasses methods of treating a mammals having any of a variety of disease states, including:
diseases treated by direct neuronal protection, such as ischemia including focal and global ischemia, spinal injuries, head trauma, and neurological diseases such as Alzheimer's and Huntington's chorea;
diseases treated by inhibition of sodium ion, such as uraemic and hyponatraemic encephalopathy; and
diseases treated with calcium channel antagonists, including:
  diseases treated by inhibiting cerebrovascular vasospasm and by cerebrovascular vasodilation, such as migraine, stroke, vasospasm due to subarachnoid hemorrhage, epilepsy or epileptic psychotic symptoms, and cerebrovascular ischemia induced by cocaine abuse; and
  cardiovascular diseases, such as hypertension, angina, stable and unstable angina, Prinzmetal angina, arrhythmia, thrombosis, embolism, and congestive heart failure such as chronic or acute cardiac failure; and
  ischemia of lower legs due to peripheral vascular disease, e.g., intermittent claudication;
  spasms of smooth muscle: such as the ureter, the bladder, uterine cramps, diuresis, and irritable bowel syndrome; and
  uses during surgery: such as bypass grafts, angiography, angioplasty, organ preservation during transplant, hypertensive crisis, or post operative hypertension,
by administering a therapeutically effective amount of compound of Formula A to a mammal in need thereof.

Another aspect of the present invention encompasses pharmaceutical formulations comprising a compound of Formula A and a pharmaceutically acceptable excipient.

DETAILED DESCRIPTION OF THE INVENTION

Definitions

The numbering of the piperazines and diazepines of the present invention is as follows:

$$\underset{R^1}{\overset{H}{\underset{\diagdown}{N}}}\underset{\underset{2}{\overset{1}{\phantom{N}}}\;\underset{4}{\overset{5}{\phantom{N}}}}{\overset{R^2}{=}}\underset{\underset{R^3}{|}}{CH}-(CH_2)_n-N_4\underset{(CH_2)_m}{\diagdown}{}_1N-(CH_2)_q-\underset{\underset{R^5}{|}}{\overset{R^4}{|}}{CH}$$

The compounds of the invention will be named using the above-shown numbering system as 1-[optionally mono- or di-aryl]-alkyl-4-[(optionally 2- and/or 5-substituted-imidazolyl)-optionally-substituted-alkyl]-piperazines and -diazepines. Some representative compounds are named as follows:

the compound of Formula A where $R^1$ is 4-methylphenyl, $R^2$ is methyl, $R^3$ is hydrogen, $R^4$ is phenyl, $R^5$ is phenyl, m is 2, n is 0 and q is 0, is named "1-diphenylmethyl-4-[(2-(4-methylphenyl)- 5-methyl-1H-imidazol-4-yl)methyl]piperazine";

the compound of Formula A where $R^1$ is 4-methylphenyl, $R^2$ is hydrogen, $R^3$ is hydrogen, $R^4$ is phenyl, $R^5$ is phenyl, m is 2, n is 0 and q is 0, is named "1-diphenylmethyl-4-[(2-(4-methylphenyl)- 1H-imidazol-4-yl)methyl]piperazine";

the compound of Formula A where $R^1$ is phenyl, $R^2$ is methyl, $R^3$ is methyl, $R^4$ is phenyl, $R^5$ is phenyl, m is 2, n is 0 and q is 0, is named "1-diphenylmethyl-4-[1-(2-phenyl-5-methyl- 1H-imidazol-4-yl)ethyl]piperazine";

the compound of Formula A where $R^1$ is cyclohexyl, $R^2$ is methyl, $R^3$ is ethyl, $R^4$ is phenyl, $R^5$ is 2,3-dimethoxyphenyl, m is 2, n is 2 and q is 2, is named "1-[3-phenyl-3-(2,3-dimethoxyphenyl)propyl]- 4-[3-(2-cyclohexyl-5-methyl-1H-imidazol- 4-yl)pentyl]piperazine";

the compound of Formula A where $R^1$ is phenyl, $R^2$ is methyl, $R^3$ is hydroxy, $R^4$ is phenyl, $R^5$ is phenyl, m is 2, n is 1 and q is 0, is named "1-diphenylmethyl-4-[2-(2-phenyl-5-methyl- 1H-imidazol-4-yl)-2-hydroxyethyl]piperazine";

the compound of Formula A where $R^1$ is phenyl, $R^2$ is methyl, $R^3$ is hydrogen, $R^4$ is 4-fluorophenyl, $R^5$ is 4-fluorophenyl, m is 2, n is 0 and q is 3, is named "1-[4,4-di-(4-fluorophenyl)-butyl]- 4-[(2-phenyl-5-methyl-1H-imidazol-4-yl)-methyl]piperazine"; and the compound of Formula A where $R^1$ is 2,4-dihydroxyphenyl, $R^2$ is methyl, $R^3$ is hydrogen, $R^4$ is phenyl, $R^5$ is phenyl, m is 3, n is 0 and q is 0, is named "1-diphenylmethyl-4-[ (2-(2,4-dihydroxyphenyl)-5-methyl-1H-imidazol-4-yl)-methyl]diazepine".

Compounds of the invention where $R^3$ is lower alkyl or hydroxy, and/or where $R^4$ and $R^5$ are different and neither is hydrogen will have one or two chiral centers and may display optical activity. The optical isomers may be separated using conventional methods. For purposes of the present invention, any compound having optical activity shall include each individual isomer as well as mixtures thereof.

As used herein, the term "alkyl" means a branched or unbranched saturated hydrocarbon radical having from 1–6 carbon atoms. Examples include methyl, ethyl, propyl, t-butyl, n-pentyl and n-hexyl, and the like.

As used herein, the term "cycloalkyl" means a saturated carbocyclic hydrocarbyl ring having from 3 to 7 ring carbon atoms, one of which has a single available valence. Examples include cyclopropyl, cyclopentyl, cyclohexyl, and the like.

As used herein, the term "alkoxy" means the group —OR wherein R is alkyl as defined above. Examples include methoxy, ethoxy, propoxy, t-butoxy, n-pentyloxy, n-hexyloxy, and the like.

As used herein, the term "lower" modifies alkyl and alkoxy and refers to those radicals having four carbon atoms or less.

As used herein, the term "halo" means fluoro, chloro, bromo and/or iodo.

As used herein, the term "aryl" refers to phenyl and optionally mono-, di-, and tri-substituted phenyl, wherein the optional substituents are lower alkyl, lower alkoxy, hydroxy, trifluoromethyl, or halo. Examples include 2-chlorophenyl, 2-trifluoromethylphenyl, 4-methoxyphenyl, 4-chlorophenyl, 3,4-dimethoxyphenyl, 4-hydroxyphenyl, 4-methylphenyl, 3-t-butylphenyl, 4-hexylphenyl, and the like.

As used herein, the term "treatment" or "treating" means any treatment of a disease in a mammal, and includes:

(i) preventing the disease, i.e., causing the clinical symptoms of the disease not to develop;

(ii) inhibiting the disease, i.e., arresting the development of clinical symptoms; and/or (iii) relieving the disease, i.e., causing the regression of clinical symptoms.

As used herein, the terms "pharmaceutically acceptable salts" refers to those salts that retain biological effectiveness and properties of the neutral parent compounds and which are not biologically or otherwise undesirable. Pharmaceutically acceptable acid addition salts may be formed with inorganic acids, such as hydrochloric acid, hydrobromic acid, sulfuric acid, nitric acid, phosphoric acid, and the like, and with organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, para-toluenesulfonic acid, salicylic acid, and the like. The salts may be single or multiple salts of one or more anions, e.g., from the above-described acids.

Presently Preferred Embodiments

Presently preferred embodiments of this invention are compounds of Formula A wherein $R^1$ is aryl; further preferred are the compounds where $R^1$ is aryl, m is 2; q is 0; n is 0; $R^2$ is methyl; and $R^3$ is hydrogen. The pharmaceutically acceptable salts of these compounds are also preferred, especially the mono-, di- and tri-hydrochlorides, and the tartrate salts.

Particularly preferred are those compounds where $R^1$ is 4-methylphenyl or phenyl and $R^4$ and $R^5$ are the same, e.g., both phenyl.

Other preferred compounds include those where $R^1$ is aryl or cycloalkyl; especially those where $R^3$ is lower alkyl, particularly methyl and isopropyl; m is 2; q is 0; n is 0; and $R^1$, $R^4$ and $R^5$ are all phenyl.

Still other preferred compounds include those where q is 3; n is 0; $R^1$ is phenyl; $R^3$ hydrogen; and $R^4$ and $R^5$ are both 4-fluorophenyl.

Another preferred compound is that wherein m is 2 or 3; q is 0; n is 0; $R^1$ is phenyl; $R^2$ is methyl; $R^3$ is hydrogen; and $R^4$ and $R^5$ are both phenyl, e.g., 1-(diphenylmethyl)-4-[(2-phenyl-5-methyl-1H-imidazol- 4-yl)methyl]piperazine.

Most preferred is the compound 1-(diphenylmethyl)-4-[(2-(4-methylphenyl)-5-methyl-1H-imidazol-4-yl)methyl]piperazine and the trihydrochloride and tartrate salts thereof.

Utility and Methods of Administration

General Utility

The compounds of this invention are useful for treating mammals having a variety of vascular disease states, and have protective activity against some of the deleterious effects resultant upon cerebral ischemia.

Disease states that may be treated include:

diseases treated by direct neuronal protection, such as ischemia including focal and global ischemia, spinal injuries, head trauma, and neurological diseases such as Alzheimer's and Huntington's chorea;

diseases treated by inhibition of sodium ion, such as uraemic and hyponatraemic encephalopathy; and diseases treated with calcium channel antagonists, including:

diseases treated by inhibiting cerebrovascular vasospasm and by cerebrovascular vasodilation, such as migraine, stroke, vasospasm due to subarachnoid hemorrhage, epilepsy or epileptic psychotic symptoms, and cerebrovascular ischemia induced by cocaine abuse; and cardiovascular diseases, such as hypertension, angina, stable and unstable angina, Prinzmetal angina, arrhythmia, thrombosis, embolism, and congestive heart failure such as chronic or acute cardiac failure; and ischemia of lower legs due to peripheral vascular disease, e.g., intermittent claudication;

spasms of smooth muscle: such as the ureter, the bladder, uterine cramps, diuresis, and irritable bowel syndrome; and uses during surgery: such as bypass grafts, angiography, angioplasty, organ preservation during transplant, hypertensive crisis, or post operative hypertension.

The compounds of this invention are particularly useful for treating cerebrovascular disease states, for example, stroke.

Generally, the disease states treated with the compounds of the present invention are found in mammals, including: domestic commercial animals such as horses, cattle, sheep and pigs; domestic house animals such as dogs, cats, and the like; and particularly humans.

Activity Testing

Testing for activity in treating the above-described disease states can be undertaken in vitro and/or in vivo using assay procedures known in the literature. The following are examples of such assay procedures.

Activity for treating vascular disease states can be determined in vitro by determining selective vascular relaxant activity, and in vivo by determining general cardiovascular activity.

In vitro calcium antagonistic activity of the compounds of this invention is determined by an assay using rat aortic strip, which is a modification of that described by R. Kent, et al., *Federation Proceedings*, 40, 724 (1981). Cerebrovascular selectivity of action is determined by comparing potencies on rabbit basilar artery and rabbit ear artery using a modification of the procedure described by R. Towart, et al., *Arzneim. Forsh.*, 32(I), 338–346 (1982).

In vivo protective effects of the compounds of this invention against the deleterious effects of cerebral ischemia are determined by use of the standard gerbil brain ischemia model. This assay is a modification of that described by T. Kirino, *Brain Res.*, 239, 57–69P (1982).

General Administration

The compounds of this invention are administered at a therapeutically effective dosage, i.e., a dosage sufficient to provide treatment for the disease states previously described. Administration of the active compounds and salts described herein can be via any of the accepted modes of administration for agents that serve similar utilities.

Generally, a daily dose of from 0.02 to 50 mg/kg of body weight per day of the active compound of Formula A. Most conditions respond to treatment comprising a dosage level on the order of 0.1 to 4 mg/kilogram of body weight per day. Thus, for administration to a 70 kg person, the dosage range would be about 1.4 to 3500 mg per day, preferably about 7.0 to 280 mg per day.

Depending on the specific disease state, administration can be via any accepted systemic route, for example, via parenteral, oral, intravenous, or nasal routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula A and, in addition, may include other medicinal agents, pharmaceutical agents, carriers, adjuvants, etc.

For example, in methods of treating stroke, particularly acute ischemic stroke, an active compound of Formula A can be co-administered with one or more agents active in reducing the risk of stroke, such as aspirin or ticlopidine (preferably ticlopidine, which has been demonstrated to reduce the risk of a second ischemic event). Co-administration can be in the form of a single formulation (combining, for example, a compound of Formula A and ticlopidine with pharmaceutically acceptable excipients, optionally segregating the two active ingredients in different excipeient mixtures designed to independently control their respective release rates and durations) or by independent administration of separate formulations containing the active agents.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula A. The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

Oral Administration

The preferred manner of administration, for the conditions detailed above, is oral using a convenient daily dosage regimen which can be adjusted according to the degree of affliction. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/% and 99.99 wt/% of the compound of Formula A, but preferably such compositions will contain between 25 wt/% and about 80 wt/%.

Preferably the compositions will take the form of a pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like.

Suppositories

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/% to about 10 wt/%; preferably from about 1 wt/% to about 2 wt/%.

Liquids

Liquid pharmaceutically administerable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension. Preferred parenteral formulations are described in copending application Ser. No. 260,628, filed Oct. 21, 1988, now U.S. Pat. No. 4,973,591, incorporated herein by reference.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

Methods of Preparation

The compounds of this invention can be made as shown in Reaction Schemes I–VI, wherein $R^1$, $R^2$, $R^3$, $R^4$, and $R^5$ have the same meaning as set forth above in the Summary Of The Invention, newly introduced variable $R^6$ is lower alkyl, X is halo, and a is an integer from zero to four.

REACTION SCHEME I

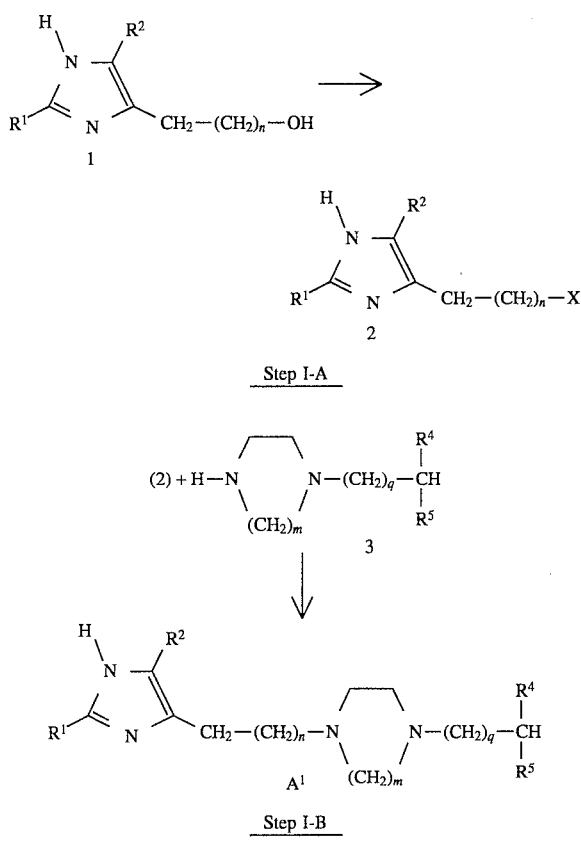

Step I-A

Step I-B

I. Preparation of Formula A Where $R^3$ is Hydrogen

Referring to Reaction Scheme I, in Step I-A a mixture of a compound of Formula 1 with an inert hydrocarbon solvent (for example, benzene, toluene, chloroform and the like) is contacted with a slight excess of a halogenating agent, for example, a thionyl halide (such as thionyl chloride), to produce the corresponding alkyl halide derivative, compound of Formula 2. Compounds of Formula 1 are obtained using the procedures of Dziuron and Sunack [*Arch, Pharm.*, 306, 347 (1973) and *Arch. Pharm.*, 307, 46 (1973)]; Imbach et al., *Bull. Soc. Chim. France*, 3, 1059 (1971); Cornforth and Huang, *J. Chem. Soc.*, (1948) 731–735; Ewins, *J. Chem. Soc.*, 99 2052 (1911); or U.S. Pat. No. 4,107,307. The reaction is conducted at a temperature from about 0° C. to the reflux temperature of the solvent, but preferably between about 40° C. and 65° C.

In Step I-B, the compound of Formula 2 is contacted with a compound of Formula 3 in a condensation reaction, for example, at a temperature from about 25°–80° C., preferably at the reflux temperature of the solvent system used.

The 1-substituted piperazines of Formula 3 are commercially available or can be made by the procedures of Hamlin, et al., *J. Am, Chem. Soc.*, 71, 31 (1949) or Cheeseman, *J. Chem Soc.*, (1975), 115–123. Diazepine analogs (i.e., those compounds where m is 3) can be made by this method using diazepine as the starting material instead of piperazine. An alkaline solution is made by dissolving a compound of Formula 3 in a polar solvent (for example, methanol, ethanol, or a mixture such as ethanol and water, methanol and water, acetone in water, dimethylfozmamide in water, isopropanol in water, tetrahydrofuran in water; in the ratio of from about 10:90 to about 90:10, preferably about 60:40), and adding a base (such as sodium hydroxide, potassium hydroxide, sodium carbonate, sodium bicarbonate, potassium carbonate, potassium bicarbonate, and the like). The alkaline solution is heated to reflux.

A solution of the compound of Formula 2 dissolved in the same polar solvent is added dropwise to the refluxing solution of the compound of Formula 3. After about 1 to 24 hours, preferably about 2 to 5 hours, the condensed product of Formula $A^1$ is separated from the reaction mixture either by precipitation or evaporation under reduced pressure. The reaction mixture is allowed to stand at room temperature, for example, for about 8 to 24 hours, or overnight. If the product precipitated, the resulting crystals are removed by filtration and recrystallized in an alcohol, preferably methanol or ethanol giving the free base of Formula $A^1$. If the product is an oil, the oil is washed with water and dissolved in diethyl ether. Acid is added and the product is precipitated as the acid addition salt using ethanol.

The free base can be converted to the salt by dissolving the free base in a suitable organic solvent, such as ethanol or ether, and extracting with acidic aqueous solution. The use of heat may be required to dissolve the free base, depending upon the acid chosen.

The salt can be converted back to the free base by suspending it, for example in ether, and adding an excess of a dilute aqueous base, such as potassium carbonate, until the salt dissolves. The organic layer is separated, washed with water, dried and evaporated to yield the free base.

The salt of a compound of formula A can be converted to another salt by methods known in the art for interconversion of salts.

REACTION SCHEME II

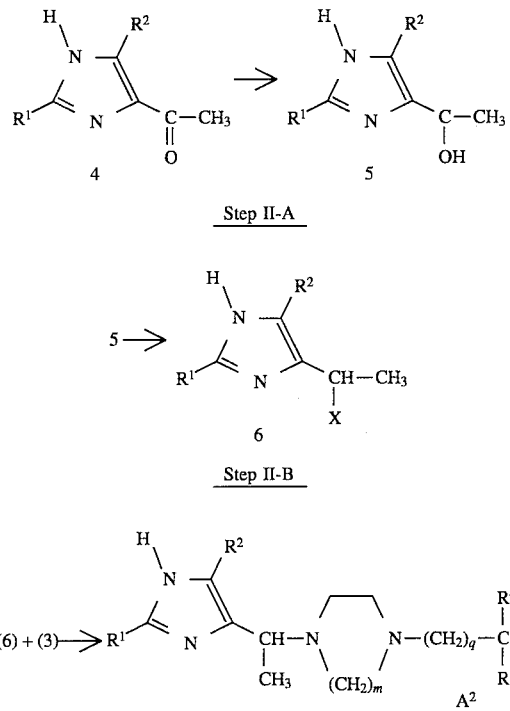

Step II-A

Step II-B

Step II-C

II. Preparation of Formula A Where $R^3$ is Methyl and n is 0

Referring to Reaction Scheme II, in Step II-A a compound of Formula 4 [obtained using the procedure of Vecchio, et al., *Chim. Ind. (Milan)*, 58(6), 451 (1976) or of Haruki, et al., *Nippon Kagaku Zasshiu*, 86(9), 942–946 (1965) (Japan)] is reduced by contacting it with a reducing agent, such as a hydride (for example, potassium borohydride, or lithium aluminum hydride) in an alcoholic solution (for example, methanol, ethanol, isopropanol, and the like). The solution is stirred for about 2 to 16 hours, e.g., overnight, and the resulting solid material, of Formula 5, is removed by filtration (using reduced pressure if necessary), washed, dried and used in the next step without further purification.

In Step II-B, the crude compound of Formula 5 is dissolved in an inert solvent (for example, chloroform, dichloromethane, benzene, toluene, and the like). A halogenating agent, such as thionyl chloride, is added to the solution and the resulting mixture is heated at reflux for a period of time between 1 and 10 hours, preferably between about 4 and 6 hours. After cooling, the solvent is removed under reduced pressure and the residue is triturated in acetone to give a compound of Formula 6.

In Step II-C, the compound of Formula 6 and a compound of Formula 3 are reacted together under the conditions described in Step I-B to give a compound according to Formula $A^2$. An oil product may be separated, dissolved in ether, and acidified to precipitate. The reaction time is about 1 to 24 hours, preferably about 4 to 5 hours.

REACTION SCHEME III

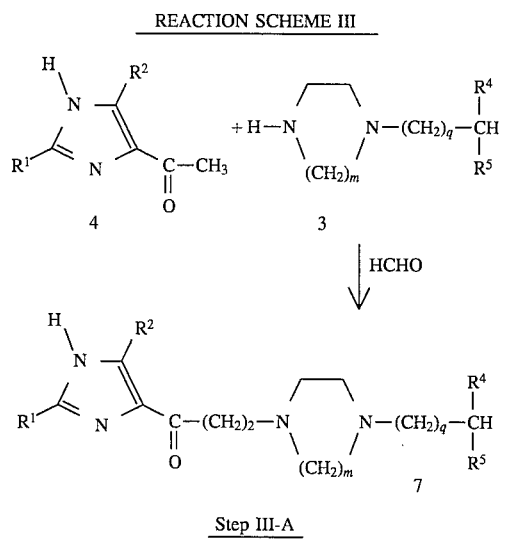

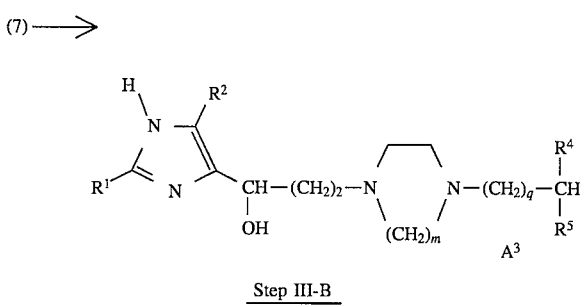

Step III-B

III. Preparation of Formula A Where $R^3$ is Hydroxyl and n is 2

Referring to Reaction Scheme III, in Step III-A a methyl ketone, such as a compound of Formula 4, an amine, such as a compound of Formula 3, and formaldehyde are reacted together under the conditions typically used for a Mannich reaction, to give a compound of Formula 7. Thus, the ketone of Formula 7 is dissolved in a solvent such as water, methanol, ethanol, or acetic acid and formaldehyde is introduced. The amine is then added and the reaction mixture is refluxed. If necessary a small amount of an acid such as hydrochloric acid, may be introduced to assure that the reaction mixture is not basic.

In Step III-B, the compound of Formula 7 is reduced under conditions similar to those described in Step II-A, to give a compound of Formula $A^3$.

REACTION SCHEME IV

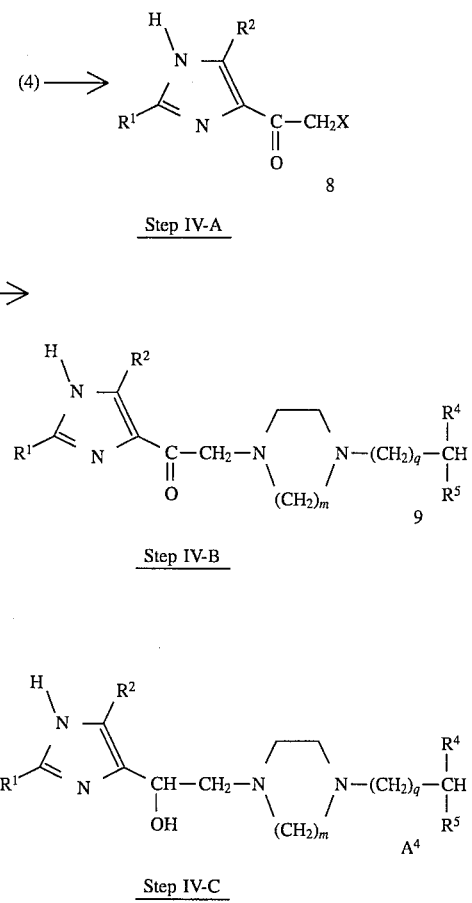

IV. Preparation of Formula A Where $R^3$ is Hydroxyl and n is 1

Referring to Reaction Scheme IV, in Step IV-A a compound of Formula 4 is halogenated, by contacting it with a halogenating agent, for example, thionyl halide, under conditions similar to those described in Step I-A, to give a compound of the Formula 8.

In Step IV-B, a compound of Formula 8 and a compound of Formula 3 are condensed by contacting them under conditions similar to those described for Step I-B, to give a compound of Formula 9.

In Step IV-C, a compound of Formula 9 is reduced, by contacting it with a reducing agent under conditions similar to those described for Step III-A to give a compound of Formula $A^4$.

REACTION SCHEME V

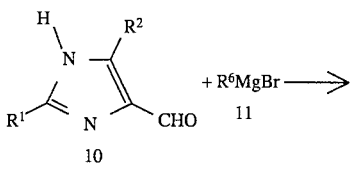

-continued
REACTION SCHEME V

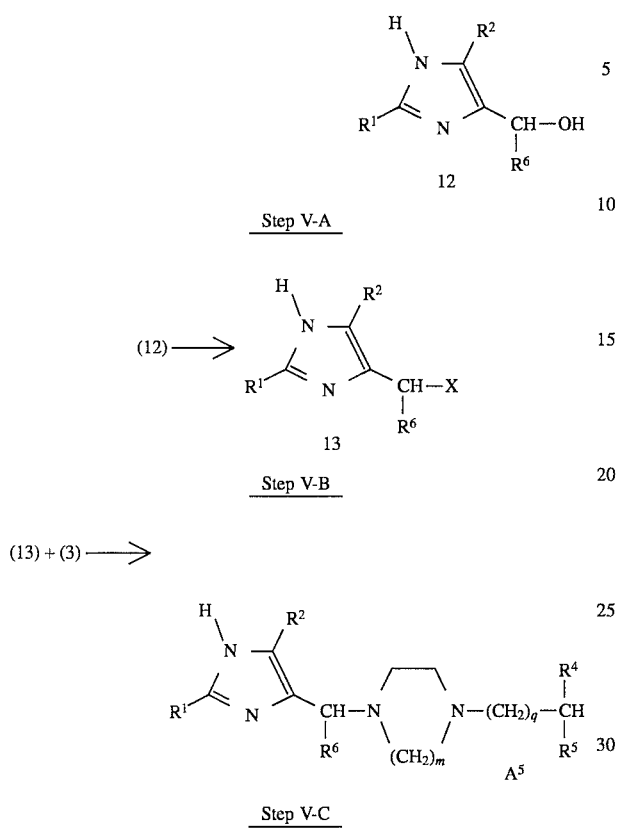

Step V-A

Step V-B

Step V-C

V. Preparation of Formula A Where $R^3$ is Lower Alkyl

Referring to Reaction Scheme V, in Step V-A, the Grignard reagent of a lower alkyl halide, the compound of Formula 11, is contacted with an imidazole compound of Formula 10 [obtained using the procedure of Cornforth and Huang, *J. Chem Soc.*, (1948), 731–735] in a neutral solvent (for example, diethyl ether, tetrahydrofuran, tetrahydropyran, and the like) and refluxed for between 15 minutes and 2 hours, preferably between 20 minutes and 40 minutes, and is then cooled and poured into ice water. The aqueous layer is extracted with a suitable organic solvent, such as diethyl ether. When the solvent is removed under reduced pressure, a residue is formed that can be recrystallized in ethanol yielding a compound of Formula 12.

In Step V-B, a compound of Formula 12 is halogenated under conditions similar to those described for Step I-A, to give a compound of Formula 13.

In Step V-C, a compound of Formula 13 and a compound of Formula 3 are contacted under conditions similar to those described for Step I-B, to give a compound of Formula $A^5$.

REACTION SCHEME VI

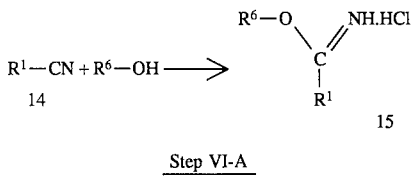

Step VI-A

-continued
REACTION SCHEME VI

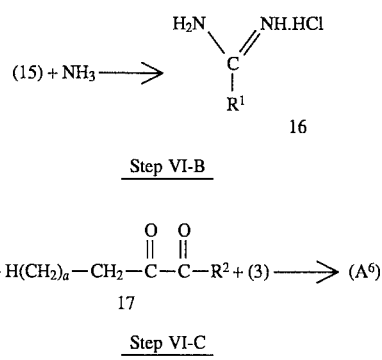

Step VI-B $$(16) + H(CH_2)_a-CH_2-\overset{O}{\overset{\|}{C}}-\overset{O}{\overset{\|}{C}}-R^2 + (3) \longrightarrow (A^6)$$
17

Step VI-C

Preferred Method For Compounds Where n is Zero

High yields of the compounds of Formula A where n is zero, can be obtained by the synthetic method illustrated in Reaction Scheme VI. It is preferred for the synthesis of compounds where n is zero, $R^2$ is lower alkyl and $R^3$ is lower alkyl having one carbon atom less than $R^2$ (or $R^3$ is hydrogen when $R^2$ is methyl).

Notably, the last step of this process can be completed in a single reaction vessle and produce a crystalline form of the end product, which requires no recrystallization or milling before incorporation into a pharmaceutical formulation. Thus, the process is preferred for its improved yield, the reduced time and manpower requirements for carrying it out, and the crystalline nature of the resulting product.

Referring to Reaction Scheme VI, in Step VI-A, a nitrile of Formula 14 (preferably 4-methylbenzonitrile) is dissolved in an alcohol (preferably methanol or ethanol, more preferably 99% ethanol), the solution is saturated with an excess of dry HCl gas and stirred at room temperature for from 1 to 24 hours, preferably overnight. The imine precipitate (the compound of Formula 15) is filtered, washed and dried. A second crop of precipitate can be collected by placing the mother liquors in a freezer overnight, after which the resulting precipitate is washed and dried.

In Step VI-B, the imine of Formula 15 is added slowly with stirring to an alcohol (preferably methanol), which is saturated with ammonia. Once the imine is dissolved, the solution is stirred at room temperature for from 1 to 24 hours, preferably overnight. The solution is reduced by ⅔ volume under vacuum, then diluted with 3 times its volume with isopropylacetate. An amidine precipitate (the compound of Formula 16) is formed, filtered and dried.

In Step VI-C, the amidine of Formula 16 is then dissolved in alcohol (preferably methanol or ethanol, more preferably 99% ethanol). A slight molar excess of a substituted dione compound of Formula 17 (preferably wherein $H(CH_2)_a-CH_2$ is the same as $R^2$, most preferably butanedione) is added dropwise and the reaction mixture refluxed for 1 to 40 hours, preferably 15 to 25 hours, more preferably about 20 hours. The mixture is then cooled to 15° to 40° C., preferably about 30° C., a compound of Formula 3 [preferably N-(diphenyl-methyl)piperazine] is added, followed by the addition of water, a base (such as sodium hydroxide, potassium hydroxide, sodium carbonate, sodium bicarbonate, potassium carbonate, potassium bicarbonate, and the like, preferably sodium hydroxide) and a slight molar excess of a metal halide (such as lithium bromide, lithium iodide, lithium chloride, potassium bromide, preferably lithium bromide). Any insoluble material is removed by filtration and the solution is refluxed for 1 to 10 hours, preferably 4 to 6 hours. The reaction mixture is cooled and stirred at room temperature for 1 to 24 hours, preferably overnight, to form a precipitate (the compound of Formula $A^6$, i.e., Formula A where n is zero).

Optionally, in cases where the resulting product contains in excess of, e.g., about 0.2% of mineral impurities, a reslurring step can be performed, wherein the precipitate is then filtered, and poured into an alcohol/water mixture (such as methanol/water, ethanol/water, isopropanol/water in a ratio of from 10:90 to about 90:10, preferably 60:40). The solution is warmed to 50° to 80° C., preferably about 70° C., for 15 minutes to 4 hours, preferably about 1 hour, then cooled, and the precipitate filtered and dried.

Compounds prepared by the above-described preferred process of the invention may be identified (e.g., using mass spectroscopy, NMR spectroscopy, or preferably, atomic absorption spectroscopy) by the presence of a slight, but detectable amount of a lithium compound used in the process as a reagent (e.g., LiBr) or produced in it as a side product (e.g., LiOH). While it is well known that pharmaceuticals must meet pharmacopoeia standards before approval and/or marketing, and that synthetic reagents or side products should not exceed the limits prescribed by pharmacopoeia standards, final compounds prepared by a process of the present invention may have minor, but detectable, amounts of such materials present. It is important to monitor the purity pharmaceutical compounds for the presence of such materials, which presence is additionally disclosed as a method of detecting use of a process of the invention.

Preferred Processes

The compounds of the present invention can be prepared by the following last steps, in which non-essential substituents are not referenced, but will be apparent from reference to the foregoing reaction schemes:

a 4-haloalkyl-1H-imidazole (or a salt thereof) is condensed with an alkyl-4-piperazine to give a compound according to Formula A where m is 2;

a 4-haloalkyl-1H-imidazole (or a salt thereof) is condensed with an alkyl-4-diazepine to give a compound according to Formula A where m is 3;

a 4-(1-halo-$C_2$–$C_4$-alkyl)-1H-imidazole (or a salt thereof) is condensed with an alkyl-4-piperazine to give, a compound according to Formula A where m is 2, and $R^3$ is lower alkyl;

a 4-(1-halo-$C_2$–$C_4$-alkyl)-1H-imidazole (or a salt thereof) is condensed with an alkyl-4-diazepine to give a compound according to Formula A where m is 3, and $R^3$ is lower alkyl;

a 1-alkyl-4-[(1H-imidazol-4-yl)-1-oxo-alkyl]-piperazine is reduced to give the corresponding compound according to Formula A where m is 2, and $R^3$ is hydroxy;

a 1-alkyl-4-[(1H-imidazol-4-yl)-1-oxo-alkyl]-diazepine is reduced to give the corresponding compound according to Formula A where m is 3, and $R^3$ is hydroxy;

exemplifying the preparation of a further substituted compound, a 2-(aryl)-4-(ω-haloalkyl)-5-alkyl-1H-imidazole (or a salt thereof) is condensed with a diaryl-alkyl- 4-piperazine to give a compound according to Formula A where $R^1$ is aryl, $R^2$ is alkyl, $R^3$ is hydrogen, $R^4$ and $R^5$ are aryl, m is 2, n is 0–2, and q is 0–3;

a substituted amidine is reacted with a substituted dione and a substituted-4-piperazine or a substituted- 4-diazepine in the presence of lithium to give a compound of Formula A;

a pharmaceutically acceptable acid is reacted with a compound of Formula A to form the corresponding acid addition salt of Formula A;

a pharmaceutically acceptable acid addition salt of Formula A is converted to another pharmaceutically acceptable acid addition salt of Formula A; or an acid addition salt of Formula A is reacted with a base to form the corresponding free base compound of Formula A.

EXAMPLES

The following examples and preparations are given to enable those skilled in the art to more clearly understand and to practice the present invention. They should not be considered as a limitation on the scope of the invention, but merely as being illustrative and representative thereof.

PREPARATION 1

Preparation of Compound of Formula 1

A solution of 1 mole (117.5 g) of tolunitrile in 50 ml absolute ethanol (99%) was saturated with dry HCl gas then kept under stirring at room temperature overnight. A first crop of crystals was collected by filtration then mother liquors were concentrated and placed in a freezer (–18° C.) for 16 hours. A second crop was obtained, giving an overall yield of 80%. Without further purification, the crude product (160 g) was put in 200 ml $NH_3$-saturated methanol, portionwise with stirring. After complete dissolution the reaction medium was left at room temperature overnight then ⅓ of the methanol was removed under reduced pressure. The resulting solution was diluted with 200 ml of isopropyl-acetate and left to crystallize at room temperature for one day. The desired toluamidine hydrochloride was recovered by filtration, dried overnight at 50° C. and used without further purification in the next step (77 g of a white powder, 90% yield).

77 g of the above benzamidine hydrochloride were dissolved in 200 ml of water then one equivalent of butanedione was added. The pH was adjusted to 7 with 2N sodium hydroxide and the reaction medium was left for two hours at 0° C. The white solid formed was filtered off and washed with acetone. The crude product (93 g) was dissolved in 500 ml of 10N HCl then the solution was heated to 100° C. with stirring for 6 hours. After cooling, the white solid formed was recovered by filtration and recrystallized from water to give 65 g of 2-(4-methylphenyl)-5-methyl-4-hydroxymethyl-1H-imidazole, melting point, 167°–169° C.

This 4-hydroxymethyl-1H-imidazole was then reacted with a thionyl halide using the procedures set forth above to form the 2-(4-methylphenyl)-4-chloro-methyl- 5-methyl-1H-imidazole hydrochloride used in Example 1.

EXAMPLE 1

1-Diphenylmethyl-4-[(2-(4-methylphenyl)-
5-methyl-1H-imidazol-4-yl)methyl]piperazine and
Derivatives Thereof 1A, Formula A Where $R^1$ is 4-Methylphenyl; $R^2$ is Methyl: $R^3$ is Hydrogen: $R^4$ and $R^5$ are Phenyl; m is 2: n is 0: and q is 0

50 Grams (0.2 mol) of 2-(4-methylphenyl)-4-chloromethyl- 5-methyl-1H-imidazole hydrochloride dissolved in 200 ml of a mixture of ethanol:water 6:4 were added dropwise to a refluxing solution of 55 grams (0.2 mol) of N-(diphenylmethyl)piperazine and 24 grams (0.6 mol) sodium hydroxide in 200 ml of a mixture of ethanol:water 6:4. After 2 to 3 hours 1-diphenylmethyl-4-[(2-(4-methylphenyl)- 5-methyl-1H-imidazol-4-yl)methyl]piperazine precipitated from the reaction mixture. After having left the crystals standing at room temperature, they were removed by filtration and recrystallized from methanol to give the free base which melted at 220°–222° C.

The free base was converted to its acid addition salt by the process taught in Example 6.

1B. Formula A Varying $R^1$ and $R^2$

Similarly, following the procedure of Part A above, but replacing 2-(4-methylphenyl)-4-chloromethyl-5-methyl-1H-imidazole hydrochloride with:

2-phenyl-4-chloromethyl-5-methyl-1H-imidazole hydrochloride;

2-methyl-4-chloromethyl-5-methyl-1H-imidazole hydrochloride;

2-t-butyl-4-chloromethyl-5-methyl-1H-imidazole hydrochloride;

2-(3-methylphenyl)-4-chloromethyl-5-methyl-1H-imidazole hydrochloride;

2-(2-methylphenyl)-4-chloromethyl-5-methyl-1H-imidazole hydrochloride;

2-(4-t-butylphenyl)-4-chloromethyl-5-methyl-1H-imidazole hydrochloride;

2-(3-t-butylphenyl)-4-chloromethyl-5-methyl-1H-imidazole hydrochloride;

2-(2-t-butylphenyl)-4-chloromethyl-5-methyl-1H-imidazole hydrochloride;

2-(4-chlorophenyl)-4-chloromethyl-5-methyl-1H-imidazole hydrochloride;

2-(3-chlorophenyl)-4-chloromethyl-5-methyl-1H-imidazole hydrochloride;

2-(2-chlorophenyl)-4-chloromethyl-5-methyl-1H-imidazole hydrochloride;

2-(4-methoxyphenyl)-4-chloromethyl-5-methyl-1H-imidazole hydrochloride;

2-(3-methoxyphenyl)-4-chloromethyl-5-methyl-1H-imidazole hydrochloride 2-(2-methoxyphenyl)-4-chloromethyl-5-methyl-1H-imidazole hydrochloride;

2-(2-methylphenyl)-4-chloromethyl-5-ethyl-1H-imidazol hydrochloride;

2-(4-methylphenyl)-4-chloromethyl-5-t-butyl-1H-imidazole hydrochloride;

2-(4-methylphenyl)-4-chloromethyl-1H-imidazole hydrochloride 2-(3,4-dimethoxyphenyl)-4-bromomethyl-5-methyl-1H-imidazole hydrochloride;

2,5-di-(4-methylphenyl)-4-chloromethyl-1H-imidazole hydrochloride;

2-(cyclopropyl)-4-chloromethyl-5-methyl-1H-imidazole hydrochloride;

4-chloromethyl-5-methyl-1H-imidazole hydrochloride; and 4-chloromethyl-5-(3-methoxyphenyl)-1H-imidazole hydrochloride, there is obtained:

1-diphenylmethyl-4-[(2-phenyl-5-methyl-1 H-imidazol-4-yl)methyl]piperazine, the trihydrochloride salt of which has a melting point of 214° C.;

1-diphenylmethyl-4-[(2,5-dimethyl-1H-imidazol- 4-yl)methyl]piperazine, the trihydrochloride salt of which has a melting point of about 225° C.;

1-diphenylmethyl-4-[(2-t-butyl-5-methyl-1H-imidazol-4-yl)methyl]piperazine;

1-diphenylmethyl-4-[(2-(3-methylphenyl)- 5-methyl-1H-imidazol-4-yl)methyl]piperazine;

1-diphenylmethyl-4-[(2-(2-methylphenyl)- 5-methyl-1H-imidazol-4-yl)methyl]piperazine;

1-diphenylmethyl-4-[(2-(4-t-butylphenyl)- 5-methyl-1H-imidazol-4-yl)methyl]piperazine;

1-diphenylmethyl-4-[ (2-(3-t-butylphenyl)- 5-methyl-1H-imidazol-4-yl)methyl]piperazine;

1-diphenylmethyl-4-[ (2-(2-t-butylphenyl)- 5-methyl-1H-imidazol-4-yl)methyl]piperazine;

1-diphenylmethyl-4-[ (2-(4-chlorophenyl)- 5-methyl-1H-imidazol-4-yl)methyl]piperazine, the trihydrochloride salt of which has a melting point of about 216° C.;

1-diphenylmethyl-4-[(2-(3-chlorophenyl)- 5-methyl-1H-imidazol-4-yl)methyl]piperazine, the trihydrochloride salt of which has a melting point of about 215° C.;

1-diphenylmethyl-4-[(2-(2-chlorophenyl)- 5-methyl-1H-imidazol-4-yl)methyl]piperazine;

1-diphenylmethyl-4-[(2-(4-methoxyphenyl)- 5-methyl-1H-imidazol-4-yl)methyl]piperazine, the trihydrochloride salt of which has a melting point of about 225° C.;

1-diphenylmethyl-4-[(2-(3-methoxyphenyl)- 5-methyl-1H-imidazol-4-yl)methyl]piperazine;

1-diphenylmethyl-4-[ (2-(2-methoxyphenyl)- 5-methyl-1H-imidazol-4-yl)methyl piperazine;

1-diphenylmethyl-4-[ (2-(2-methylphenyl)- 5-ethyl-1H-imidazol-4-yl)methyl] piperazine;

1-diphenylmethyl-4-[ (2-(4-methylphenyl)- 5-t-butyl-1H-imidazol-4-yl)methyl] piperazine;

1-diphenylmethyl-4-[ (3-(4-methylphenyl)- 1H-imidazol-4-yl)methyl] piperazine;

1-diphenylmethyl-4-[ (2-(2,4-dimethoxyphenyl)- 5-methyl-1H-imidazol-4-yl)methyl]piperazine, the trihydrochloride salt of which has a melting point of 230° C.;

1-diphenylmethyl-4-[(2,5-di-(4-methylphenyl)-1H-imidazol- 4-yl)methyl]piperazine;

1-diphenylmethyl-4-[(2-(cyclopropyl)-5-methyl-1H-imidazol- 4-yl)methyl]piperazine;

1-diphenylmethyl-4-[(5-methyl-1H-imidazol-4-yl)-methyl piperazine; and 1-diphenylmethyl-4-[(5-(3-methoxyphenyl)-1-H-imidazol- 4-yl)methyl]piperazine.

1C. Formula A Varying q, $R^4$ and $R^5$

Similarly, following the procedure of Part A above, but replacing N-(diphenylmethyl)piperazine with:

N-[di-(2-methylphenyl)methyl]piperazine;

N-[di-(3-methylphenyl)methyl]piperazine;

N-[di-(4-methylphenyl)methyl]piperazine;

N-[di-(2-t-butylphenyl)methyl]piperazine;

N-[di-(3-t-butylphenyl)methyl]piperazine;

N-[di-(4-t-butylphenyl)methyl]piperazine;

N-[di-(2-methoxyphenyl)methyl]piperazine;

N-[di-(3-methoxyphenyl)methyl]piperazine;

N-[di-(4-methoxyphenyl)methyl]piperazine;

N-[di-(2-chlorophenyl)methyl]piperazine;

N-[di-(3-chlorophenyl)methyl]piperazine;

N-[di-(4-chlorophenyl)methyl]piperazine;

N-[di-(4-fluorophenyl)methyl]piperazine;

N-benzylpiperazine;

N-[1-(4-chlorophenyl)-1-(phenyl)methyl]piperazine;

N-(2,2-diphenylethyl)piperazine;

N-[3-(phenyl)-3-(4-methoxyphenyl)propyl]piperazine; and

N-(4,4-diphenylbutyl)piperazine, there is obtained:

1-[ di-(2-methylphenyl)methyl]-4-[ (2-(4-methylphenyl)-5-methyl-1H-imidazol-4-yl)methyl]piperazine;

1-[di-(3-methylphenyl)methyl]-4-[(2-(4-methylphenyl)-5-methyl-1H-imidazol-4-yl)methyl] piperazine;

1-[di-(4-methylphenyl)methyl]-4-[(2-(4-methylphenyl)-5-methyl-1H-imidazol-4-yl)methyl]piperazine;

1-[di-(2-t-butylphenyl)methyl]-4-[ (2-(4-methylphenyl)-5-methyl-1H-imidazol-4-yl)methyl]piperazine;

1-[di-(3-t-butylphenyl)methyl]-4-[(2-(4-methylphenyl)-5-methyl-1H-imidazol-4-yl)methyl]piperazine;

1-[ di-(4-t-butylphenyl)methyl]-4-[(2-(4-methylphenyl)-5-methyl-1H-imidazol-4-yl)methyl]piperazine;

1-[ di-(2-methoxyphenyl)methyl]-4-[ (2-(4-methylphenyl)- 5-methyl-1H-imidazol-4-yl)methyl]piperazine;

1-[ di-(3-methoxyphenyl)methyl]-4-[ (2-(4-methylphenyl)- 5-methyl-1H-imidazol-4-yl)methyl]piperazine;

1-[di-(4-methoxyphenyl)methyl]-4-[ (2-(4-methylphenyl)- 5-methyl-1H-imidazol-4-yl)methyl]piperazine;

1-[di-(2-chlorophenyl)methyl]-4-[(2-(4-methylphenyl)-5-methyl-1H-imidazol-4-yl)methyl]piperazine;

1-[di-(3-chlorophenyl)methyl]-4-[(2-(4-methylphenyl)-5-methyl-1H-imidazol-4-yl)methyl]piperazine;

1-[di-(4-chlorophenyl)methyl]-4-[(2-(4-methylphenyl)-5-methyl-1H-imidazol-4-yl)methyl]piperazine, the trihydrochloride salt of which has a melting point of about 225° C.;

1-[di-(4-fluorophenyl)methyl]-4-[(2-(4-methylphenyl)-5-methyl-1H-imidazol-4-yl)methyl]piperazine, the trihydrochloride salt of which has a melting point of about 210° C.;

1-benzyl-4-[(2-(4-methylphenyl)-5-methyl-1H-imidazol-4-yl)methyl]piperazine;

1-[1-(4-chlorophenyl)-1-(phenyl)methyl]-4-[(2-(4-methylphenyl)- 5-methyl-1H-imidazol-4-yl)methyl]piperazine;

1-(2,2-diphenylethyl)-4-[(2-(4-methylphenyl)- 5-methyl-1H-imidazol-4-yl)methyl]piperazine;

1-[ 3-(phenyl)-3-(4-methyoxyphenyl)propyl]-4-[ (2-(4-methylphenyl)- 5-methyl-1H-imidazol-4-yl)methyl] piperazine; and 1-(4,4-diphenylbutyl)-4-[ (2-(4-methylphenyl)- 5-methyl-1H-imidazol-4-yl)methyl] piperazine.

1D. Formula A Varying $R^1$; $R^2$; $R^4$; $R^5$ and q

Similarly, by following the procedures of Parts B and C above, other compounds of Formula A where $R^3$ is hydrogen, m is 2, and n is 0 are obtained, such as:

1-diphenylmethyl-4-[(2-n-butyl-5-methyl-1H-imidazol-4-yl)methyl]piperazine, the trihydrochloride salt of which has a melting point of about 205° C.;

1-diphenylmethyl-4-[(2-(3-trifluoromethylphenyl)- 5-methyl-1H-imidazol-4-yl)methyl]piperazine, the trihydrochloride salt of which has a melting point of about 210° C.;

1-diphenylmethyl-4-[(2-phenyl-1H-imidazol-4-yl)methyl] piperazine, the fumarate salt of which has a melting point of 170° C.;

1-diphenylmethyl-4-[(5-methyl-1H-imidazol-4-yl)methyl] piperazine, the trihydrochloride salt of which has a melting point of about 205° C.;

1-methyl-4-[(2-phenyl-5-methyl-1H-imidazol- 4-yl)methyl]piperazine, the trihydrochloride salt of which has a melting point of about 215° C.;

1-di-(4-chlorophenyl)methyl-4-[(2-phenyl-5-methyl-1H-imidazol-4-yl)methyl]piperazine, the trihydrochloride salt of which has a melting point of 220° C.;

1-[-di-(4-fluorophenyl)butyl]-4-[(2-phenyl- 5-methyl-1H-imidazol-4-yl)methyl]piperazine, the trihydrochloride salt of which has a melting point of 198° C.; and 1-benzyl-4-[(2-phenyl-5-methyl-1H-imidazol-4-yl)-methyl] piperazine, the trihydrochloride salt of which has a melting point of 238° C.

1E. Formula A Varying m

Similarly, by following the procedures of Parts A–D above, but replacing the piperazines there-used with the corresponding diazepines, the compounds of Formula A wherein m is 3 are obtained.

For example, substituting 2-phenyl-4-chloromethyl-5-methyl- 1H-imidazole hydrochloride for 2-(4-methylphenyl)- 4-chloromethyl-5-methyl-1H-imidazole hydrochloride, and by substituting diphenylmethyl-4-diazepine for diphenylmethyl- 4-piperazine, there is obtained 1-diphenylmethyl-4-[ (2-phenyl-5-methyl-1H-imidazol-4-yl)methyl] diazepine, the trihydrochloride salt of which has a melting point of about 205° C.

EXAMPLE 2

1-Diphenylmethyl-4-[ 1-(2-phenyl-5-methyl-1H-imidazol- 4-yl)ethyl]piperazine and Derivatives Thereof 2A. Formula 5 where $R^1$ is Phenyl: and $R^2$ is Methyl 32 Grams (0.59 mol) of potassium borohydride were added portionwise to a solution of 30 g (0.15 mol) of 2-phenyl-4-acetyl-5-methylimidazole in 1500 ml of MeOH. After stirring overnight, a solid material was removed by filtration, then the solvent was evaporated under reduced pressure to give 27 g of 2-phenyl-4-(1-hydroxyethyl)- 5-methylimidazole. The crude compound thus isolated was used without further purification.

2B. Formula 6 Where $R^1$ is Phenyl; $R^2$ is Methyl; and X is Chloro

27 Grams (0.13 mol) of 2-phenyl-4-(1-hydroxyethyl)-5-methylimidazole were dissolved in 700 ml of chloroform with 44 ml (0.6 mol) of thionyl chloride and refluxed for 5 hours. After cooling, the mixture was evaporated, the residue triturated in acetone, thereby giving, in approximately stoichiometric yield, 2-phenyl-4-(1-chloroethyl)- 5-methylimidazole hydrochloride, m.p. 190° C.

2C. Formula 6 Varying $R^1$, $R^2$, and the Length of Alkyl at Position 4 of the Imidazole Similarly, following the procedures of Part A and B above, but replacing 2-phenyl-4-acetyl-5-methylimidazole with:

2-(phenyl)-4-(2-methylpropanoyl)-5-methylimidazole;

2-(3-methylphenyl)-4-acetyl-5-methylimidazole;

2-(2-methylphenyl)-4-acetyl-5-methylimidazole;

2-(4-t-butylphenyl)-4-acetyl-5-methylimidazole 2-(3-t-butylphenyl)-4-acetyl-5-methylimidazole 2-(2-t-butylphenyl)-4-acetyl-5-methylimidazole 2-(4-chlorophenyl)-4-acetyl-5-methylimidazole;

2-(3-chlorophenyl)-4-acetyl-5-methylimidazole;

2-(2-chlorophenyl)-4-acetyl-5-methylimidazole;

2-(4-methoxyphenyl)-4-acetyl-5-methylimidazole;

2-(3-methoxyphenyl)-4-acetyl-5-methylimidazole;

2-(2-methoxyphenyl)-4-acetyl-5-methylimidazole;

2-(2-methylphenyl)-4-acetyl-5-ethylimidazole;

2-(cyclopropyl)-4-acetyl-5-phenylimidazole;

2-(4-methylphenyl)-4-acetyl-5-t-butylimidazole; and 2-(4-methylphenyl)-4-acetylimidazole, there is obtained:

2-(phenyl)-4-(1-chloro-2-methylpropyl)-5-methylimidazole hydrochloride;

2-(3-methylphenyl)-4-(1-chloroethyl)-5-methylimidazole hydrochloride;

2-(2-methylphenyl)-4-(1-chloroethyl)-5-methylimidazole hydrochloride;

2-(4-t-butylphenyl)-4-(1-chloroethyl)-5-methylimidazole hydrochloride;

2-(3-t-butylphenyl)-4-(1-chloroethyl)-5-methylimidazole hydrochloride;

2-(2-t-butylphenyl)-4-(1-chloroethyl)-5-methylimidazole hydrochloride;

2-(4-chlorophenyl)-4-(1-chloroethyl)-5-methylimidazole hydrochloride;

2-(3-chlorophenyl)-4-(1-chloroethyl)-5-methylimidazole hydrochloride;

2-(2-chlorophenyl)-4-(1-chloroethyl)-5-methylimidazole hydrochloride;

2-(4-methoxyphenyl)-4-(1-chloroethyl)-5-methylimidazole hydrochloride;

2-(3-methoxyphenyl)-4-(1-chloroethyl)-5-methylimidazole hydrochloride;

2-(2-methoxyphenyl)-4-(1-chloroethyl)-5-methylimidazole hydrochloride;

2-(2-methylphenyl)-4-(1-chloroethyl)-5-ethylimidazole hydrochloride;

2-(cyclopropyl)-4-(1-chloroethyl)-5-phenylimidazole hydrochloride;

2-(4-methylphenyl)-4-(1-chloroethyl)-5-t-butylimidazole hydrochloride; and 2-(4-methylphenyl)-4-(1-chloroethyl)-imidazole hydrochloride.

2D. Formula A Where $R^1$ is Phenyl; $R^2$ is Methyl; $R^3$ is Methyl; $R^4$ and $R^5$ are Phenyl; m is 2; n is 0; and q is 0

14 Grams (0.052 mol) of N-(diphenylmethyl)piperazine and 6 grams (0.15 mol) of sodium hydroxide were dissolved in 180 ml of a mixture of ethanol :water 60:40. The mixture was heated to reflux, then 2-phenyl-4-(1-chloroethyl)- 5-methylimidazole hydrochloride in 180 milliliters of ethanol:water 60:40 were added dropwise. After 4 to 5 hours under reflux, the reaction mixture was allowed to cool to room temperature. The oil that separated was washed twice with water, then dissolved in ether and hydrochloric acid was added. The precipitate was recrystallized from ethanol to give 1-diphenylmethyl- 4-[1-(2-phenyl-5-methyl-1H-imidazol-4-yl)ethyl]piperazine trihydrochloride (55% yield), which melted at 215° C.

2E. Formula A Where $R^3$ is Methyl; $R^4$ and $R^5$ are Phenyl: m is 2; n is 0; g is 0; and Varying $R^1$ and $R^2$ Similarly, following the procedure of Part D above, but replacing 2-phenyl-4-(1-chloroethyl)-5-methylimidazole hydrochloride with:

2-(phenyl)-4-(1-chloro-2-methylpropyl)-5-methylimidazole hydrochloride;

2-(phenyl)-4-(1-chloroethyl)-5-methylimidazole hydrochloride;

2-methyl-4-(1-chloroethyl)-5-methylimidazole hydrochloride;

2-t- butyl-4-(1-chloroethyl)-5-methylimidazole hydrochloride;

2-(3-methylphenyl)-4-(1-chloroethyl)-5-methylimidazole hydrochloride;

2-(2-methylphenyl)-4-(1-chloroethyl)-5-methylimidazole hydrochloride;

2-(4-t-butylphenyl)-4-(1-chloroethyl)-5-methylimidazole hydrochloride;

2-(3-t-butylphenyl)-4-(1-chloroethyl)-5-methylimidazole hydrochloride;

2-(2-t-butylphenyl)-4-(1-chloroethyl)-5-methylimidazole hydrochloride;

2-(4-chlorophenyl)-4-(1-chloroethyl)-5-methylimidazole hydrochloride;

2-(3-chlorophenyl)-4-(1-chloroethyl)-5-methylimidazole hydrochloride;

2-(2-chlorophenyl)-4-(1-chloroethyl)-5-methylimidazole hydrochloride;

2-(4-methoxyphenyl)-4-(1-chloroethyl)-5-methylimidazole hydrochloride;

2-(3-methoxyphenyl)-4-(1-chloroethyl)-5-methylimidazole hydrochloride;

2-(2-methoxyphenyl)-4-(1-chloroethyl)-5-methylimidazole hydrochloride;

2-(2-methylphenyl)-4-(1-chloroethyl)-5-ethylimidazole hydrochloride;

2-(cyclopropyl)-4-(1-chloroethyl)-5-phenylimidazole hydrochloride;

2-(4-methylphenyl)-4-(1-chloroethyl)-5-t-butylimidazole hydrochloride; and 2-(4-methylphenyl)-4-(1-chloroethyl)-imidazole hydrochloride, there is obtained:

1-diphenylmethyl-4-[1-(2-phenyl-5-methyl- 1H-imidazol-4-yl)ethyl]piperazine trihydrochloride;

1-diphenylmethyl-4-[1-(2-methyl-5-methyl- 1H-imidazol-4-yl)ethyl]piperazine trihydrochloride;

1-diphenylmethyl-4-[1-(2-t-butyl-5-methyl- 1H-imidazol-4-yl)ethyl]piperazine trihydrochloride;

1-diphenylmethyl-4-[1-(2-(3-methylphenyl)-5-methyl-1-imidazol-4-yl)ethyl]piperazine trihydrochloride;

1-diphenylmethyl-4-[1-(2-(2-methylphenyl)-5-methyl-1H-imidazol-4-yl)ethyl]piperazine trihydrochloride;

1-diphenylmethyl-4-[1-(2-(4-t-butylphenyl)-5-methyl-1H-imidazol-4-yl)ethyl]piperazine trihydrochloride;

1-diphenylmethyl-4-[1-(2-(3-t-butylphenyl)-5-methyl-1H-imidazol-4-yl)ethyl]piperazine trihydrochloride;

1-diphenylmethyl-4-[1-(2-(2-t-butylphenyl)-5-methyl-1H-imidazol-4-yl)ethyl]piperazine trihydrochloride;

1-diphenylmethyl-4-1-(2-(4-chlorophenyl)-5-methyl-1H-imidazol-4-yl)ethyl]piperazine trihydrochloride;

1-diphenylmethyl-4-[ 1-(2-(3-chlorophenyl)-5-methyl-1H-imidazol-4-yl)ethyl]piperazine trihydrochloride;

1-diphenylmethyl-4-[ 1-(2-(2-chlorophenyl)-5-methyl-1H-imidazol-4-yl)ethyl]piperazine trihydrochloride;

1-diphenylmethyl-4-[ 1-(2-(4-methoxyphenyl)-5-methyl-1H-imidazol-4-yl)ethyl]piperazine trihydrochloride;

1-diphenylmethyl-4-[ 1-(2-(3-methoxyphenyl)-5-methyl-1H-imidazol-4-yl)ethyl]piperazine trihydrochloride;

1-diphenylmethyl-4-[1-(2-(2-methoxyphenyl)-5-methyl-1H-imidazol-4-yl)ethyl]piperazine trihydrochloride;

1-diphenylmethyl-4-[1-(2-(2-methylphenyl)-5-ethyl-1H-imidazol-4-yl)ethyl]piperazine trihydrochloride;

1-diphenylmethyl-4-[ 1-(2-(2-cyclopropyl)-5-phenyl-1H-imidazol-4-yl)ethyl]piperazine trihydrochloride;

1-diphenylmethyl-4-[ 1-(2-(4-methylphenyl)-5-t-butyl-1H-imidazol-4-yl)ethyl]piperazine trihydrochloride; and 1-diphenylmethyl-4-[ 1-(2-(4-methylphenyl)-1H-imidazol- 4-yl)ethyl]piperazine trihydrochloride.

2F. Formula A Where $R^1$ is Phenyl; $R^2$ is Methyl; $R^3$ is Methyl; m is 2; n is 0; and Varying q, $R^4$ and $R^5$ Similarly, following the procedure of Part D above, but replacing N-(diphenylmethyl)piperazine with:

N-[di-(2-methylphenyl)methyl]piperazine;
N-[di-(3-methylphenyl)methyl]piperazine;
N-[di-(4-methylphenyl)methyl]piperazine;
N-[di-(2-t-butylphenyl)methyl]piperazine;
N-[di-(3-t-butylphenyl)methyl]piperazine;
N-[di-(4-t-butylphenyl)methyl]piperazine;
N-[di-(2-methoxyphenyl)methyl]piperazine;
N-[di-(3-methoxyphenyl)methyl]piperazine;
N-[di-(4-methoxyphenyl)methyl]piperazine;
N-[di-(2-chlorophenyl)methyl]piperazine;
N-[di-(3-chlorophenyl)methyl]piperazine;
N-[di-(4-chlorophenyl)methyl]piperazine;
N-[di-(4-fluorophenyl)methyl]piperazine;
N-benzylpiperazine;

N-[1-(4-chlorophenyl)-1-(phenyl)methyl]piperazine;
N-(2,2-diphenylethyl)piperazine;
N-[3-(phenyl)-3-(4-methoxyphenyl)propyl]piperazine; and
N-(4,4-diphenylbutyl)piperazine,
there is obtained:

1-[di-(2-methylphenyl)methyl]-4-[1-(2-phenyl- 5-methyl-1H-imidazol-4-yl)ethyl]piperazine trihydrochloride;

1-[di-(3-methylphenyl)methyl]-4-[1-(2-phenyl- 5-methyl-1H-imidazol-4-yl)ethyl]piperazine trihydrochloride;

1-[di-(4-methylphenyl)methyl]-4-[1-(2-phenyl- 5-methyl-1H-imidazol-4-yl)ethyl]piperazine trihydrochloride;

1-[di-(2-t-butylphenyl)methyl]-4-[1-(2-phenyl- 5-methyl-1H-imidazol-4-yl)ethyl]piperazine trihydrochloride;

1-[di-(3-t-butylphenyl)methyl]-4-[1-(2-phenyl- 5-methyl-1H-imidazol-4-yl)ethyl]piperazine trihydrochloride;

1-[di-(4-t-butylphenyl)methyl]-4-[1-(2-phenyl- 5-methyl-1H-imidazol-4-yl)ethyl]piperazine trihydrochloride;

1-[di-(2-methoxyphenyl)methyl]-4-[1-(2-phenyl- 5-methyl-1H-imidazol-4-yl)ethyl]piperazine trihydrochloride;

1-[di-(3-methoxyphenyl)methyl]-4-[1-(2-phenyl- 5-methyl-1H-imidazol-4-yl)ethyl]piperazine trihydrochloride;

1-[di-(4-methoxyphenyl)methyl]-4-[1-(2-phenyl- 5-methyl-1H-imidazol-4-yl)ethyl]piperazine trihydrochloride;

1-[di-(2-chlorophenyl)methyl]-4-[1-(2-phenyl- 5-methyl-1H-imidazol-4-yl)ethyl]piperazine trihydrochloride;

1-[di-(3-chlorophenyl)methyl]-4-[1-(2-phenyl- 5-methyl-1H-imidazol-4-yl)ethyl]piperazine trihydrochloride;

1-[di-(4-chlorophenyl)methyl]-4-[1-(2-phenyl- 5-methyl-1H-imidazol-4-yl)ethyl]piperazine trihydrochloride;

1-[di-(4-fluorophenyl)methyl]-4-[1-(2-phenyl- 5-methyl-1H-imidazol-4-yl)ethyl]piperazine trihydrochloride;

1-benzyl-4-[1-(2-phenyl-5-methyl-1H-imidazol-4-yl)ethyl] piperazine trihydrochloride;

1-[(4-chlorophenyl)-1-(phenyl)methyl]-4-[1-(2-phenyl-5-methyl-1H-imidazol-4-yl)ethyl]piperazine trihydrochloride;

1-(2,2-diphenylethyl)-4-[1-(2-phenyl-5-methyl-1H-imidazol- 4-yl)ethyl]piperazine trihydrochloride;

1-[3-(phenyl)-3-(4-methoxyphenyl)propyl]-4-[1-(2-phenyl- 5-methyl-1H-imidazol-4-yl)ethyl]piperazine trihydrochloride; and 1-(4,4-diphenylbutyl)-4-[1-(2-phenyl-5-methyl- 1H-imidazol-4-yl)ethyl]piperazine trihydrochloride.

2G. Formula A Where $R^3$ is Methyl; m is 2; n is 0; and Varying $R^1$; $R^2$; $R^4$; $R^5$ and q Similarly, by following the procedures of Parts E and F above, other compounds of Formula A where $R^3$ is methyl, m is 2, and n is 0 are obtained, such as:

1-benzyl-4-[1-(2-methyl-5-ethyl-1H-imidazol-4-yl)-ethyl] piperazine trihydrochloride;

1-[(4-chlorophenyl)-1-(phenyl)methyl]-4-[1-(2-phenyl-5-(4-methylphenyl)-1H-imidazol-4-yl)ethyl]piperazine trihydrochloride;

1-(2,2-diphenylethyl)-4-[1-(2-cyclohexyl-5-phenyl-1H-imidazol-4-yl)ethyl]piperazine trihydrochloride;

1-[3-(phenyl)-3-(4-methoxyphenyl)propyl]-4-[1-(2-(3-methoxyphenyl)-5-propyl-1H-imidazol-4-yl)ethyl]piperazine trihydrochloride; and 1-(4,4-diphenylbutyl)-4-[1-(5-(2-methylphenyl)- 1H-imidazol-4-yl)ethyl]piperazine trihydrochloride.

2H. Formula A Where $R^3$ is Lower Alkyl Other Than Methyl

Similarly, following the procedure of Part D above, but replacing 2-phenyl-4-(1-chloroethyl)-5-methylimidazole hydrochloride with:

2-phenyl-4-(1-chloropropyl)-5-methylimidazole hydrochloride; and 2-phenyl-4-(1-chlorobutyl)-5-methylimidazole hydrochloride, there is obtained:

1-diphenylmethyl-4-[1-(2-phenyl-5-methyl-1H-imidazol-4-yl)propyl]piperazine trihydrochloride; and 1-diphenylmethyl-4-[1-(2-phenyl-5-methyl-1H-imidazol-4-yl)butyl]piperazine trihydrochloride.

2I. Formula A Varying m

Similarly, by following the procedures of Parts A–H above, but replacing the piperazines there-used with the corresponding diazepines, the compounds of Formula A wherein m is 3 are obtained.

EXAMPLE 3

1-Diphenylmethyl-4-[2-(2-phenyl-5-methyl-1H-imidazol-4-yl)-2-hydroxyethyl]piperazine trihydrochloride and Derivatives Thereof 3A. Formula 9 Where $R^1$ is Phenyl; $R^2$ is Methyl; $R^4$ and $R^5$ are Phenyl; m is 2; and u is 0

10 Grams (0.036 mol) of 2-phenyl-4-(2-bromoethanoyl)-5-methyl-1H-imidazole and 8.5 grams (0.034 mol) of N-(diphenylmethyl)piperazine and 5 grams (0.036 mol) of potassium carbonate were added to 300 ml of ethanol. The mixture was refluxed under stirring overnight. After cooling, the salts were removed by filtration and the solvent was removed under reduced pressure. The residue was extracted by dichloromethane and washed twice with water. The organic layer was dried over sodium sulfate and evaporated. Trituration of the residue with ethanol gave a white precipitate, 1-diphenylmethyl-4-[2-(2-phenyl- 5-methyl-1H-imidazol-4-yl)-2-oxoethyl]piperazine, which was used in the next reaction step without further purification.

3B. TriHCl Salt of Formula A Where $R^1$ is Phenyl; $R^2$ is Methyl; $R^3$ is hydroxy; $R^4$ and $R^5$ are phenyl; m is 2; n is 1; and q is 0

6 Grams of 1-diphenylmethyl-4-[2-(2-phenyl- 5-methyl-1H-imidazol-4-yl)-2-oxoethyl]piperazine was dissolved in 100 ml of methanol. The reaction was cooled to 5° C. and then 2 grams (0.05 mol) of sodium borohydride was added portionwise. After stirring for 2 hours at room temperature, the mixture was evaporated off. The residue was extracted with dichloromethane and washed with water. Then the organic layer was dried over sodium sulphate and the solvent removed under reduced pressure. The crude material was then dissolved in diethyloxide and hydrochloric acid was added. The white precipitate was then removed by filtration and dried to give 1-diphenylmethyl-4-[ 2-(2-phenyl-5-methyl-1H-imidazol- 4-yl)-2-hydroxyethyl]piperazine trihydrochloride, which melted at 200° C.

3C. TriHCl Salt of Formula A Where $R^3$ is Hydroxy; $R^4$ and $R^5$ are Phenyl; m is 2; n is 1; a is 0; and Varying $R^1$ and $R^2$ Similarly, following the procedures of Parts A and B above, but replacing 2-phenyl-4-(2-bromo-ethanoyl)-5-methyl- 1H-imidazole with:

2-(3-methylphenyl)-4-(2-bromoethanoyl)-5-methyl-1H-imidazole;

2-(2-methylphenyl)-4-(2-bromoethanoyl)-5-methyl-1H-imidazole;

2-(4-t-butylphenyl)-4-(2-bromoethanoyl)-5-methyl-1H-imidazole;

2-(3-t-butylphenyl)-4-(2-bromoethanoyl)-5-methyl-1H-imidazole;

2-(2-t-butylphenyl)-4-(2-bromoethanoyl)-5-methyl-1H-imidazole;

2-(4-chlorophenyl)-4-(2-bromoethanoyl)-5-methyl-1H-imidazole;

2-(3-chlorophenyl)-4-(2-bromoethanoyl)-5-methyl-1H-imidazole;

2-(2-chlorophenyl)-4-(2-bromoethanoyl)-5-methyl-1H-imidazole;

2-(4-methoxyphenyl)-4-(2-bromoethanoyl)-5-methyl-1H-imidazole;

2-(3-methoxyphenyl)-4-(2-bromoethanoyl)-5-methyl-1H-imidazole;

2-(2-methoxyphenyl)-4-(2-bromoethanoyl)-5-methyl-1H-imidazole;

2-(2-methylphenyl)-4-(2-bromoethanoyl)-5-ethyl-1H-imidazole;

2-(cyclohexyl)-4-(2-bromoethanoyl)-5-ethyl-1H-imidazole;

2-(4-methylphenyl)-4-(2-bromoethanoyl)-5-t-butyl-1H-imidazole; and 2-(4-methylphenyl)-4-(2-bromoethanoyl)-1H-imidazole,
there is obtained:

1-diphenylmethyl-4-[2-(2-(3-methylphenyl)-5-methyl-1H-imidazol-4-yl)-2-hydroxyethyl]piperazine trihydrochloride;

1-diphenylmethyl-4-[2-(2-(2-methylphenyl)-5-methyl-1H-imidazol-4-yl)-2-hydroxyethyl]piperazine trihydrochloride;

1-diphenylmethyl-4-[2-(2-(4-t-butylphenyl)-5-methyl-1H-imidazol-4-yl)-2-hydroxyethyl]piperazine trihydrochloride;

1-diphenylmethyl-4-[2-(2-(3-t-butylphenyl)-5-methyl-1H-imidazol-4-yl)-2-hydroxyethyl]piperazine trihydrochloride;

1-diphenylmethyl-4-[2-(2-(2-t-butylphenyl)-5-methyl-1H-imidazol-4-yl)-2-hydroxyethyl]piperazine trihydrochloride;

1-diphenylmethyl-4-[2-(2-(4-chlorophenyl)-5-methyl-1H-imidazol-4-yl)-2-hydroxyethyl]piperazine trihydrochloride;

1-diphenylmethyl-4-[2-(2-(3-chlorophenyl)-5-methyl-1H-imidazol-4-yl)-2-hydroxyethyl]piperazine trihydrochloride;

1-diphenylmethyl-4-[2-(2-(2-chlorophenyl)-5-methyl-1H-imidazol-4-yl)-2-hydroxyethyl]piperazine trihydrochloride;

1-diphenylmethyl-4-[2-(2-(4-methoxyphenyl)-5-methyl-1H-imidazol-4-yl)-2-hydroxyethyl]piperazine trihydrochloride;

1-diphenylmethyl-4-[2-(2-(3-methoxyphenyl)-5-methyl-1H-imidazol-4-yl)-2-hydroxyethyl]piperazine trihydrochloride;

1-diphenylmethyl-4-[2-(2-(2-methoxyphenyl)-5-methyl-1H-imidazol-4-yl)-2-hydroxyethyl]piperazine trihydrochloride;

1-diphenylmethyl-4-[2-(2-(2-methylphenyl)-5-ethyl-1H-imidazol-4-yl)-2-hydroxyethyl]piperazine trihydrochloride;

1-diphenylmethyl-4-[2-(2-cyclohexyl-5-ethyl-1H-imidazol-4-yl)-2-hydroxyethyl]piperazine trihydrochloride;

1-diphenylmethyl-4-[2-(2-(4-methylphenyl)-5-t-butyl-1H-imidazol-4-yl)-2-hydroxyethyl]piperazine trihydrochloride; and 1-diphenylmethyl-4-[2-(2-(4-methylphenyl)- 1H-imidazol-4-yl)-2-hydroxyethyl]piperazine trihydrochloride.

3D. TriHCl Salt of Formula A Where $R^1$ is Phenyl; $R^2$ is Methyl; $R^3$ is Hydroxy; m is 2; n is 1; q is 0; and Varying $R^4$ and $R^5$ Similarly, following the procedures of Parts A and B above, but replacing N-(diphenylmethyl)piperazine with:
N-[di-(2-methylphenyl)methyl]piperazine;
N-[di-(3-methylphenyl)methyl]piperazine;
N-[di-(4-methylphenyl)methyl]piperazine;
N-[di-(2-t-butylphenyl)methyl]piperazine;
N-[di-(3-t-butylphenyl)methyl]piperazine;
N-[di-(4-t-butylphenyl)methyl]piperazine;
N-[di-(2-methoxyphenyl)methyl]piperazine;
N-[di-(3-methoxyphenyl)methyl]piperazine;
N-[di-(4-methoxyphenyl)methyl]piperazine;
N-[di-(2-chlorophenyl)methyl]piperazine;
N-[di-(3-chlorophenyl)methyl]piperazine;
N-[di-(4-chlorophenyl)methyl]piperazine;
N-[di-(4-fluorophenyl)methyl]piperazine;
N-benzylpiperazine;
N-[1-(4-chlorophenyl)-1-(phenyl)methyl]piperazine;
N-(2,2-diphenylethyl)piperazine;
N-[3-(Phenyl)-3-(4-methoxyphenyl)propyl]piperazine; and
N-(4,4-diphenylbutyl)piperazine,
there is obtained:

1-[di-(2-methylphenyl)methyl]-4-[2-(2-phenyl- 5-methyl-1H-imidazol-4-yl)-2-hydroxyethyl]piperazine trihydrochloride;

1-[di-(3-methylphenyl)methyl]-4-[2-(2-phenyl- 5-methyl-1H-imidazol-4-yl)-2-hydroxyethyl]piperazine trihydrochloride;

1-[di-(4-methylphenyl)methyl]-4-[2-(2-phenyl- 5-methyl-1H-imidazol-4-yl)-2-hydroxyethyl]piperazine trihydrochloride;

1-[di-(2-t-butylphenyl)methyl]-4-[2-(2-phenyl- 5-methyl-1H-imidazol-4-yl)-2-hydroxyethyl]piperazine trihydrochloride;

1-[di-(3-t-butylphenyl)methyl]-4-[2-(2-phenyl- 5-methyl-1H-imidazol-4-yl)-2-hydroxyethyl]piperazine trihydrochloride;

1-[di-(4-t-butylphenyl)methyl]-4-[2-(2-phenyl- 5-methyl-1H-imidazol-4-yl)-2-hydroxyethyl]piperazine trihydrochloride;

1-[di-(2-methoxyphenyl)methyl]-4-[2-(2-phenyl- 5-methyl-1H-imidazol-4-yl)-2-hydroxyethyl]piperazine trihydrochloride;

1-[di-(3-methoxyphenyl)methyl]-4-[2-(2-phenyl- 5-methyl-1H-imidazol-4-yl)-2-hydroxyethyl]piperazine trihydrochloride;

1-[di-(4-methoxyphenyl)methyl]-4-[2-(2-phenyl- 5-methyl-1H-imidazol-4-yl)-2-hydroxyethyl]piperazine trihydrochloride;

1-[di-(2-chlorophenyl)methyl]-4-[2-(2-phenyl- 5-methyl-1H-imidazol-4-yl)-2-hydroxyethyl]piperazine trihydrochloride;

1-[di-(3-chlorophenyl)methyl]-4-[2-(2-phenyl- 5-methyl-1H-imidazol-4-yl)-2-hydroxyethyl]piperazine trihydrochloride;

1-[di-(4-chlorophenyl)methyl]-4-[2-(2-phenyl- 5-methyl-1H-imidazol-4-yl)-2-hydroxyethyl]piperazine trihydrochloride;

1-[di-(4-fluorophenyl)methyl]-4-[2-(2-phenyl- 5-methyl-1H-imidazol-4-yl)-2-hydroxyethyl]piperazine trihydrochloride;

1-benzyl-4-[2-(2-phenyl-5-methyl-1H-imidazol-4-yl)ethyl-] piperazine trihydrochloride;

1-[(4-chlorophenyl)-1-(phenyl)methyl]-4-[2-(2-phenyl-5-methyl-1H-imidazol-4-yl)-2-hydroxyethyl]piperazine trihydrochloride;

1-(2,2-diphenylethyl)-4-[2-(2-phenyl-5-methyl-1H-imidazol-4-yl)-2-hydroxyethyl]piperazine trihydrochloride;

1-[3-(phenyl)-3-(4-methoxyphenyl)propyl]-4-[2-(2-phenyl- 5-methyl-1H-imidazol-4-yl)-2-hydroxyethyl]piperazine trihydrochloride; and 1-(4,4-diphenylbutyl)-4-[2-(2-phenyl-5-methyl- 1H-imidazol-4-yl)-2-hydroxyethyl]piperazine trihydrochloride.

3E. TriHCl Salt of Formula A Where $R^3$ is Hydroxy; m is 2; n is 1 or 2; and Varying $R^1$; $R^2$; $R^4$; $R^5$ and q Similarly, by following the procedures of Parts C and D above, other compounds of Formula A where $R^3$ is hydroxy, m is 2, and n is 1 or 2 are obtained, such as:

1-[(4-chlorophenyl)-1-(phenyl)methyl]-4-[2-(2-methyl-5-phenyl-1H-imidazol-4-yl)-2-hydroxyethyl]piperazine trihydrochloride;

1-[(4-chlorophenyl)-1-(phenyl)methyl]-4-[3-(2-phenyl-5-methyl-1H-imidazol-4-yl)-3-hydroxypropyl]piperazine trihydrochloride, by starting with 2-phenyl-4-(3-bromopropanoyl)- 5-methyl-1H-imidazole in part 3A;

1-(2,2-diphenylethyl)-4-[2-(2-(4-methylphenyl)- 5-methyl-1H-imidazol-4-yl)-2-hydroxyethyl]piperazine trihydrochloride;

1-[3-(phenyl)-3-(4-methoxyphenyl)propyl]-4-[2-(2-cyclopropyl- 5-ethyl-1H-imidazol-4-yl)-2-hydroxyethyl]piperazine trihydrochloride; and 1-(4,4-diphenylbutyl)-4-[2-(5-methyl-1H-imidazol-4-yl)-2-hydroxyethyl]piperazine trihydrochloride.

3F. Formula A Varying m

Similarly, by following the procedures of Parts A–E above, but replacing the piperazines there-used with the corresponding diazepines, the compounds of Formula A wherein m is 3 are obtained.

EXAMPLE 4

1-Diphenylmethyl-4-[1-(2-phenyl-5-methyl-1H-imidazol-4-yl)-2-methylpropyl]piperazine and Derivatives Thereof 4A. Formula 12 Where $R^1$ is Phenyl; $R^2$ is Methyl; and $R^6$ is Isopropyl 35 Grams (0.45 mol) of 2-chloropropane was added to 10.8 g (0.45 mol) of magnesium in 100 ml of diethyl ether. Then 55.8 g (0.3 mol) of 2-phenyl-4-formyl-5-methyl-1H-imidazole in 100 ml of THF were added. At the end of the addition, the mixture was refluxed for 30 minutes and then cooled and poured on ice water. The aqueous layer was extracted twice with 100 ml of diethyl ether. Evaporation of the solvent gave a residue which was recrystallized in ethanol to yield 40 grams of 2-phenyl- 4-(1-hydroxy-2-methylpropyl)-5-methyl-1H-imidazole, which melted at 214° C.

4B. Formula 12 Where $R^6$ is Isopropyl; and Varying $R^1$ and $R^2$

Similarly, following the procedure of Part A above, but replacing 2-phenyl-4-formyl-5-methyl-1H-imidazole with:

2-(3-methylphenyl)-5-methyl-4-formyl-1H-imidazole;

2-(2-methylphenyl)-5-methyl-4-formyl-1H-imidazole;

2-(4-t-butylphenyl)-5-methyl-4-formyl-1H-imidazole;

2-(3-t-butylphenyl)-5-methyl-4-formyl-1H-imidazole;

2-(2-t-butylphenyl)-5-methyl-4-formyl-1H-imidazole;

2-(4-chlorophenyl)-5-methyl-4-formyl-1H-imidazole;

2-(3-chlorophenyl)-5-methyl-4-formyl-1H-imidazole;

2-(2-chlorophenyl)-5-methyl-4-formyl-1H-imidazole;

2-(4-methoxyphenyl)-5-methyl-4-formyl-1H-imidazole;

2-(3-methoxyphenyl)-5-methyl-4-formyl-1H-imidazole;

2-(2-methoxyphenyl)-5-methyl-4-formyl-1H-imidazole;

2-(2-methylphenyl)-5-ethyl-4-formyl-1H-imidazole;

2-(4-methylphenyl)-5-t-butyl-4-formyl-1H-imidazole;

2-(4-methylphenyl)-4-formyl-1H-imidazole, 2-(3,4-dimethoxyphenyl) -4-formyl-5-methyl-1H-imidazole;

2,5-di-(4-methylphenyl)-4-formyl-1H-imidazole;

2-(cyclopropyl)-4-formyl-5-methyl-1H-imidazole;

2-ethyl-4-formyl-5-methyl-1H-imidazole;

4-formyl-5-phenyl-1H-imidazole; and 2-methyl-4-formyl-5-(3-methoxyphenyl)-1H-imidazole, there is obtained:

2-(3-methylphenyl)-5-methyl-4-(1-hydroxy- 2-methylpropyl)-1H-imidazole;

2-(2-methylphenyl)-5-methyl-4-(1-hydroxy- 2-methylpropyl)-1H-imidazole;

2-(4-t-butylphenyl)-5-methyl-4-(1-hydroxy- 2-methylpropyl)-1H-imidazole;

2-(3-t-butylphenyl)-5-methyl-4-(1-hydroxy- 2-methylpropyl)-1H-imidazole;

2-(2-t-butylphenyl)-5-methyl-4-(1-hydroxy- 2-methylpropyl)-1H-imidazole;

2-(4-chlorophenyl)-5-methyl-4-(1-hydroxy- 2-methylpropyl)-1H-imidazole;

2-(3-chlorophenyl)-5-methyl-4-(1-hydroxy- 2-methylpropyl)-1H-imidazole;

2-(2-chlorophenyl)-5-methyl-4-(1-hydroxy- 2-methylpropyl)-1H-imidazole;

2-(4-methoxyphenyl)-5-methyl-4-(1-hydroxy- 2-methylpropyl)-1H-imidazole;

2-(3-methoxyphenyl)-5-methyl-4-(1-hydroxy- 2-methylpropyl)-1H-imidazole;

2-(2-methoxyphenyl)-5-methyl-4-(1-hydroxy- 2-methylpropyl)-1H-imidazole;

2-(2-methylphenyl)-5-ethyl-4-(1-hydroxy- 2-methylpropyl)-1H-imidazole;

2-(4-methylphenyl)-5-t-butyl-4-(1-hydroxy- 2-methylpropyl)-1H-imidazole;

2-(4-methylphenyl)-4-(1-hydroxy-2-methylpropyl)-1H-imidazole;

2-(3,4-dimethoxyphenyl)-5-methyl-4-(1-hydroxy- 2-methylpropyl)-1H-imidazole;

2,5-di-(4-methylphenyl)-4-(1-hydroxy-2-methylpropyl)-1H-imidazole;

2-cyclopropyl-5-methyl-4-(1-hydroxy-2-methylpropyl)-1H-imidazole;

2-ethyl-5-methyl-4-(1-hydroxy-2-methylpropyl)-1H-imidazole;

4-(1-hydroxy-2-methylpropyl)-5-phenyl-1H-imidazole; and 2-methyl-5-(3-methoxyphenyl)-4-(1-hydroxy-2-methylpropyl)- 1H-imidazole.

4C. Formula 13 Where $R^1$ is Phenyl; $R^2$ is Methyl; $R^6$ is Isopropyl; and X is Chloro 27 g of 2-phenyl-4-(1-hydroxy-2-methylpropyl)- 5-methyl-1H-imidazole are dissolved in 700 ml of chloroform with 44 ml of thionyl chloride (SOCl$_2$) and refluxed for 5 hours. 2-Phenyl-5-methyl-4-(1-chloro- 2-methylpropyl)-1H-imidazole hydrochloride is isolated in quantitative yield.

4D. Formula 13 Where $R^6$ is Isopropyl; X is Chloro; and Varying $R^1$ and $R^2$ Similarly, following the procedure of Part C above, but replacing 2-phenyl-5-methyl-4-(1-hydroxy-2-methylpropyl)- 1H-imidazole with:

2-(3-methylphenyl)-5-methyl-4-(1-hydroxy- 2-methyl-propyl)-1H-imidazole;
2-(2-methylphenyl)-5-methyl-4-(1-hydroxy- 2-methyl-propyl)-1H-imidazole;
2-(4-t-butylphenyl)-5-methyl-4-(1-hydroxy- 2-methyl-propyl)-1H-imidazole;
2-(3-t-butylphenyl)-5-methyl-4-(1-hydroxy- 2-methyl-propyl)-1H-imidazole;
2-(2-t-butylphenyl)-5-methyl-4-(1-hydroxy- 2-methyl-propyl)-1H-imidazole;
2-(4-chlorophenyl)-5-methyl-4-(1-hydroxy- 2-methyl-propyl)-1H-imidazole;
2-(3-chlorophenyl)-5-methyl-4-(1-hydroxy- 2-methyl-propyl)-1H-imidazole;
2-(2-chlorophenyl)-5-methyl-4-(1-hydroxy- 2-methyl-propyl)-1H-imidazole;
2-(2-methoxyphenyl)-5-methyl-4-(1-hydroxy- 2-methyl-propyl)-1H-imidazole;
2-3-methoxyphenyl)-5-methyl-4-(1-hydroxy- 2-methyl-propyl)-1H-imidazole;
2-(2-methoxyphenyl)-5-methyl-4-(1-hydroxy- 2-methyl-propyl)-1H-imidazole;
2-(2-methylphenyl)-5-ethyl-4-(1-hydroxy- 2-methylpropyl)-1H-imidazole;
2-(4-methylphenyl)-5-t-butyl-4-(1-hydroxy-2-methylpropyl)- 1H-imidazole hydrochloride;
2-(4-methylphenyl)-4-(1-hydroxy-2-methylpropyl)-1H-imidazole hydrochloride;
2-(3,4-dimethoxyphenyl)-4-(1-hydroxy-2-methylpropyl)-5-methyl-1H-imidazole;
2,5-di-(4-methylphenyl)-4-(1-hydroxy-2-methylpropyl)-1H-imidazole;
2-cyclopropyl-5-methyl-4-(1-hydroxy-2-methylpropyl)-1H-imidazole;
2-ethyl-5-methyl-4-(1-hydroxy-2-methylpropyl)-1H-imidazole;
4-(1-hydroxy-2-methylpropyl)-5-phenyl-1H-imidazole; and
2-methyl-4-(1-hydroxy-2-methylpropyl)-5-(3-methoxyphenyl)- 1H-imidazole,
there is obtained:
2-(3-methylphenyl)-5-methyl-4-(1-chloro-2-methylpropyl)- 1H-imidazole hydrochloride;
2-(2-methylphenyl)-5-methyl-4-(1-chloro-2-methylpropyl)- 1H-imidazole hydrochloride;
2-(4-t-butylphenyl)-5-methyl-4-(1-chloro-2-methylpropyl)- 1H-imidazole hydrochloride;
2-(3-t-butylphenyl)-5-methyl-4-(1-chloro-2-methylpropyl)- 1H-imidazole hydrochloride;
2-(2-t-butylphenyl)-5-methyl-4-(1-chloro-2-methylpropyl)- 1H-imidazole hydrochloride;
2-(4-chlorophenyl)-5-methyl-4-(1-chloro-2-methylpropyl)- 1H-imidazole hydrochloride;
2-(3-chlorophenyl)-5-methyl-4-(1-chloro-2-methylpropyl)- 1H-imidazole hydrochloride;
2-(2-chlorophenyl)-5-methyl-4-(1-chloro-2-methylpropyl)- 1H-imidazole hydrochloride;
2-(4-methoxyphenyl)-5-methyl-4-(1-chloro-2-methylpropyl)- 1H-imidazole hydrochloride;
2-(3-methoxyphenyl)-5-methyl-4-(1-chloro-2-methylpropyl)- 1H-imidazole hydrochloride;
2-(2-methoxyphenyl)-5-methyl-4-(1-chloro-2-methylpropyl)- 1H-imidazole hydrochloride;
2-(2-methylphenyl)-5-ethyl-4-(1-chloro-2-methylpropyl)- 1H-imidazole hydrochloride;
2-(4-methylphenyl)-5-t-butyl-4-(1-chloro-2-methylpropyl)- 1H-imidazole hydrochloride;
2-(4-methylphenyl)-4-(1-chloro-2-methylpropyl)-1H-imidazole hydrochloride;
2-(3,4-dimethoxyphenyl)-5-methyl-4-(1-chloro-2-methylpropyl)- 1H-imidazole hydrochloride;
2,5-di-(4-methylphenyl)-4-(1-chloro-2-methylpropyl)- 1H-imidazole hydrochloride;
2-cyclopropyl-5-methyl-4-(1-chloro-2-methylpropyl)- 1H-imidazole hydrochloride;
2-ethyl-5-methyl-4-(1-chloro-2-methylpropyl)- 1H-imidazole;
4-(1-chloro-2-methylpropyl)-5-phenyl-1H-imidazole hydrochloride; and
2-methyl-5-(3-methoxyphenyl)-4-(1-chloro-2-methylpropyl)- 1H-imidazole hydrochloride.

4E. TriHCl Salt of Formula A Where $R^1$ is Phenyl; $R^2$ is Methyl; $R^3$ is Isopropyl; $R^4$ and $R^5$ are Phenyl; m is 2; n is 0; and q is 0

14 Grams (0.05 mol) of diphenylmethyl-4-piperazine and 6 grams (0.15 mol) of sodium hydroxide are dissolved in 180 ml of a mixture of ethanol:water 60:40. The mixture is heated to reflux, then 2-phenyl-5-methyl- 4-(1-chloro-2-methylpropyl)-1H-imidazole hydrochloride in 180 milliliters of ethanol:water 60:40 are added dropwise. After 4 to 5 hours under reflux, the reaction mixture is allowed to cool to room temperature. The oil that separated is washed twice with water, then dissolved in ether and hydrochloric acid is added. The precipitate is recrystallized from ethanol to give 1-diphenylmethyl- 4-[1-(2-phenyl-5-methyl-1H-imidazol-4-yl)-2-methylpropyl] piperazine trihydrochloride.

4F. TriHCl Salt of Formula A Where $R^3$ is Isopropyl; $R^4$ and $R^5$ are Phenyl; m is 2; n is 0; q is 0; and Varying $R^1$ and $R^2$ Similarly, following the procedure of Part E above, but replacing 2-phenyl-5-methyl-4-(1-chloro-2-methylpropyl- 1H-imidazole hydrochloride with:
2 -(3-methylphenyl)-5-methyl-4-(1-chloro-2-methylpropyl)- 1H-imidazole hydrochloride;
2-(2-methylphenyl)-5-methyl-4-(1-chloro-2-methylpropyl)- 1H-imidazole hydrochloride;
2-(4-t-butylphenyl)-5-methyl-4-(1-chloro-2-methylpropyl)- 1H-imidazole hydrochloride;
2-(3-t-butylphenyl)-5-methyl-4-(1-chloro-2-methylpropyl)- 1H-imidazole hydrochloride;
2-(2-t-butylphenyl)-5-methyl-4-(1-chloro-2-methylpropyl)- 1H-imidazole hydrochloride;
2-(4-chlorophenyl)-5-methyl-4-(1-chloro-2-methylpropyl)- 1H-imidazole hydrochloride;
2-(3-chlorophenyl)-5-methyl-4-(1-chloro-2-methylpropyl)- 1H-imidazole hydrochloride;
2-(2-chlorophenyl)-5-methyl-4-(1-chloro-2-methylpropyl)- 1H-imidazole hydrochloride;
2-(4-methoxyphenyl)-5-methyl-4-(1-chloro-2-methylpropyl)- 1H-imidazole hydrochloride;
2-(3-methoxyphenyl)-5-methyl-4-(1-chloro-2-methylpropyl)- 1H-imidazole hydrochloride;
2-(2-methoxyphenyl)-5-methyl-4-(1-chloro-2-methylpropyl)- 1H-imidazole hydrochloride;
2-(2-methylphenyl)-5-ethyl-4-(1-chloro-2-methylpropyl)- 1H-imidazole hydrochloride;
2-(4-methylphenyl)-5-t-butyl-4-(1-chloro-2-methylpropyl- 1H-imidazole hydrochloride;
2-(4-methylphenyl)-4-(1-chloro-2-methylpropyl)- 1H-imidazole hydrochloride;
2-(3,4-dimethoxyphenyl)-4-(1-chloro-2-methylpropyl)-5-methyl-1H-imidazole hydrochloride;
2,5-di-(4-methylphenyl)-4-(1-chloro-2-methylpropyl)- 1H-imidazole hydrochloride;

2-cyclopropyl-5-methyl-4-(1-chloro-2-methylpropyl)-1H-imidazole hydrochloride;

2-ethyl-5-methyl-4-(1-chloro-2-methylpropyl)- 1H-imidazole;

4-(1-chloro-2-methylpropyl)-5-phenyl-1H-imidazole hydrochloride; and 2-methyl-4-(1-chloro-2-methylpropyl)-5-(3-methoxyphenyl)- 1H-imidazole hydrochloride,
there is obtained:

1-diphenylmethyl-4-[1-(2-(3-methylphenyl)-5-methyl-1H-imidazol-4-yl)-2-methylpropyl]piperazine trihydrochloride;

1-diphenylmethyl-4-[1-(2-(2-methylphenyl)-5-methyl-1H-imidazol-4-yl)-2-methylpropyl]piperazine trihydrochloride;

1-diphenylmethyl-4-[1-(2-(4-t-butylphenyl)-5-methyl-1H-imidazol-4-yl)-2-methylpropyl]piperazine trihydrochloride;

1-diphenylmethyl-4-[1-(2-(3-t-butylphenyl)-5-methyl-1H-imidazol-4-yl)-2-methylpropyl]piperazine trihydrochloride;

1-diphenylmethyl-4-[1-(2-(2-t-butylphenyl)-5-methyl-1H-imidazol-4-yl)-2-methylpropyl]piperazine trihydrochloride;

1-diphenylmethyl-4-[1-(2-(4-chlorophenyl)-5-methyl-1H-imidazol-4-yl)-2-methylpropyl]piperazine trihydrochloride;

1-diphenylmethyl-4-[1-(2-(3-chlorophenyl)-5-methyl-1H-imidazol-4-yl)-2-methylpropyl]piperazine trihydrochloride;

1-diphenylmethyl-4-[1-(2-(2-chlorophenyl)-5-methyl-1H-imidazol-4-yl)-2-methylpropyl]piperazine trihydrochloride;

1-diphenylmethyl-4-[1-(2-(4-methoxyphenyl)-5-methyl-1H-imidazol-4-yl)-2-methylpropyl]piperazine trihydrochloride;

1-diphenylmethyl-4-[1-(2-(3-methoxyphenyl)-5-methyl-1H-imidazol-4-yl)-2-methylpropyl]piperazine trihydrochloride;

1-diphenylmethyl-4-[1-(2-(2-methoxyphenyl)-5-methyl-1H-imidazol-4-yl)-2-methylpropyl]piperazine trihydrochloride;

1-diphenylmethyl-4-[1-(2-(2-methylphenyl)-5-ethyl-1H-imidazol-4-yl)-2-methylpropyl]piperazine trihydrochloride;

1-diphenylmethyl-4-[1-(2-(4-methylphenyl)-5-t-butyl-1H-imidazol-4-yl)-2-methylpropyl]piperazine trihydrochloride;

1-diphenylmethyl-4-[1-(2-(4-methylphenyl)-1H-imidazol-4-yl)-2-methylpropyl]piperazine trihydrochloride;

1-diphenylmethyl-4-[1-(2-(3,4-dimethoxyphenyl)- 5-methyl-1H-imidazol-4-yl)-2-methylpropyl]piperazine trihydrochloride;

1-diphenylmethyl-4-[1-(2,5-di-(4-methylphenyl)-1H-imidazol-4-yl)-2-methylpropyl]piperazine trihydrochloride;

1-diphenylmethyl-4-[1-(2-cyclopropyl-5-methyl-1H-imidazol-4-yl)-2-methylpropyl]piperazine trihydrochloride;

1-diphenylmethyl-4-[1-(2-ethyl-5-methyl-1H-imidazol-4-yl)-2-methylpropyl]piperazine trihydrochloride;

1-diphenylmethyl-4-[1-(5-phenyl-1H-imidazol-4-yl)-2-methylpropyl]piperazine trihydrochloride; and 1-diphenylmethyl-4-[1-(2-methyl-5-(3-methoxyphenyl)-1H-imidazol-4-yl)-2-methylpropyl]piperazine trihydrochloride.

4G. Formula A Where $R^3$ is Isopropyl. Varying q, $R^4$ and $R^5$

Similarly, following the procedure of Part E above, but replacing N-(diphenylmethyl)piperazine with:
N-[di-(2-methylphenyl)methyl]piperazine;
N-[di-(3-methylphenyl)methyl]piperazine;
N-[di-(4-methylphenyl)methyl] piperazine;
N-[di-(2-t-butylphenyl)methyl]piperazine;
N-[di-(3-t-butylphenyl)methyl]piperazine;
N-[di-(4-t-butylphenyl)methyl]piperazine;
N-[di-(2-methoxyphenyl)methyl]piperazine;
N-[di-(3-methoxyphenyl)methyl]piperazine;
N-[di-(4-methoxyphenyl)methyl]piperazine;
N-[di-(2-chlorophenyl)methyl]piperazine;
N-[di-(3-chlorophenyl)methyl]piperazine;
N-[di-(4-chlorophenyl)methyl]piperazine;
N-[di-(4-fluorophenyl)methyl]piperazine;
N-benzylpiperazine;
N-[ 1-(4-chlorophenyl)-1-(phenyl)methyl piperazine;
N-(2,2-diphenylethyl)piperazine;
N-[3-(phenyl)-3-(4-methoxyphenyl)propyl]piperazine; and
N-(4,4-diphenylbutyl)piperazine,
there is obtained:

1-[di-(2-methylphenyl)methyl]-4-[1-(2-phenyl- 5-methyl-1H-imidazol-4-yl)-2-methylpropyl]piperazine trihydrochloride;

1-[di-(3-methylphenyl)methyl]-4-[1-(2-phenyl- 5-methyl-1H-imidazol-4-yl)-2-methylpropyl]piperazine trihydrochloride;

1-[di-(4-methylphenyl)methyl]-4-[1-(2-phenyl- 5-methyl-1H-imidazol-4-yl)-2-methylpropyl]piperazine trihydrochloride;

1-[di-(2-t-butylphenyl)methyl]-4-[1-(2-phenyl- 5-methyl-1H-imidazol-4-yl)-2-methylpropyl]piperazine trihydrochloride;

1-[di-(3-t-butylphenyl)methyl]-4-[1-(2-phenyl- 5-methyl-1H-imidazol-4-yl)-2-methylpropyl]piperazine trihydrochloride;

1-[di-(4-t-butylphenyl)methyl]-4-[1-(2-phenyl- 5-methyl-1H-imidazol-4-yl)-2-methylpropyl]piperazine trihydrochloride;

1-[di-(2-methoxyphenyl)methyl]-4-[1-(2-phenyl- 5-methyl-1H-imidazol-4-yl)-2-methylpropyl]piperazine trihydrochloride;

1-[di-(3-methoxyphenyl)methyl]-4-[1-(2-phenyl- 5-methyl-1H-imidazol-4-yl)-2-methylpropyl]piperazine trihydrochloride;

1-[di-(4-methoxyphenyl)methyl]-4-[1-(2-phenyl- 5-methyl-1H-imidazol-4-yl)-2-methylpropyl]piperazine trihydrochloride;

1-[di-(2-chlorophenyl)methyl]-4-[1-(2-phenyl- 5-methyl-1H-imidazol-4-yl)-2-methylpropyl] piperazine trihydrochloride;

1-[di-(3-chlorophenyl)methyl]-4-[ 1-(2-phenyl- 5-methyl-1H- imidazol-4-yl)-2-methylpropyl]piperazine trihydrochloride;

1-[di-(4-chlorophenyl)methyl] -4-[ 1-(2-phenyl- 5-methyl-1H-imidazol-4-yl)-2-methylpropyl] piperazine trihydrochloride;

1-[di-(4-fluorophenyl)methyl]-4-[1-(2-phenyl- 5-methyl-1H-imidazol-4-yl)-2-methylpropyl]piperazine trihydrochloride;

1-benzyl-4-[1-(2-phenyl-5-methyl-1H-imidazol-4-yl)-2-methylpropyl]piperazine trihydrochloride;

1-[1-(4-chlorophenyl)-1-(phenyl)methyl]-4-[1-( 2-phenyl-5-methyl-1H-imidazol-4-yl)-2-methylpropyl]piperazine trihydrochloride;

1-(2,2-diphenylethyl)-4-[1-(2-phenyl-5-methyl-1H-imidazol- 4-yl)-2-methylpropyl]piperazine trihydrochloride;

1-[3-(phenyl)-3-(4-methyoxyphenyl)propyl]-4-[1-(2-phenyl-5-methyl-1H-imidazol-4-yl)-2-methylpropyl]piperazine trihydrochloride; and 1-(4,4-diphenylbutyl)-4-[1-(2-phenyl-5-methyl-1H-imidazol-4-yl)-2-methylpropyl]piperazine trihydrochloride.

4H. TriHCl Salt of Formula A Where $R^3$ is Lower Alkyl Other Than Isopropyl

Similarly, by following the procedures of Parts A–G above, and substituting in for 2-chloropropane in Part A the following compounds:
  1-chloroethane;
  chloromethane;
  2-chlorobutane,
there are obtained the corresponding compounds where $R^3$ is, respectively, ethyl, methyl and butyl, such as:

1-diphenylmethyl-4-[1-(2-phenyl-5-methyl-1H-imidazol-4-yl) propyl]piperazine trihydrochloride;

1-diphenylmethyl-4-[1-(2-phenyl-5-methyl-1H-imidazol-4-yl) ethyl]piperazine trihydrochloride;

1-diphenylmethyl-4-[1-(2-phenyl-5-methyl-1-imidazol-4-yl) -2-methylbutyl]piperazine trihydrochloride;

1-(4,4-diphenylbutyl)-4-[ 1-(2-phenyl-5-methyl-1H-imidazol-4-yl)-2-methylbutyl]piperazine trihydrochloride;

1-[ 1-(4-chlorophenyl)-1-(phenyl)methyl]-4-[ 1( 2-phenyl-5-methyl-1H-imidazol-4-yl)propyl]piperazine trihydrochloride;

1-diphenylmethyl-4-[ 1-(2-(4-methylphenyl)-5-ethyl-1H-imidazol-4-yl)propyl]piperazine trihydrochloride; and 1-diphenylmethyl-4-[ 1-(2,5-diphenyl-1H-imidazol-4-yl)-2-methylbutyl]piperazine trihydrochloride.

4I. Formula A Varying m

Similarly, by following the procedures of Parts A–H above, but replacing the piperazines there-used with the corresponding diazepines, the compounds of Formula A wherein m is 3 are obtained.

EXAMPLE 5

1-Diphenylmethyl-4-[2-(4-methylphenyl)- 5-methyl-1H-imidazol-4-yl)methyl] piperazine and Derivatives Thereof 5A. Formula 15 Where $R^1$ is 4-Methylphenyl and $R^6$ is Ethyl A solution of 4-methylbenzonitrile in 99% ethanol was saturated with 3 equivalents of dry HCl gas and the reaction mixture was stirred overnight. The precipitate which formed was filtered and the mother liquors were placed in a freezer at −18° C. overnight. A second crop was obtained from the mother liquors. The combined crops were dried at 30° C. overnight under vacuum, giving 78% yield of ethoxy-4-methylbenzimine hydrochloride (compound of Formula 15).

5B. Formula 16 Where $R^1$ is 4-Methylphenyl

The product of step 5A was added portionwise with stirring to methanol which had been saturated with ammonia, in the ratio of 1 liter methanol to 1 kilogram of product of step A. The product of step 5A dissolved slowly and the solution was stirred overnight. Two thirds of the volume was evaporated under vacuum. The remaining solution was diluted with three times its volume of isopropylacetate. The solution was filtered and dried overnight at 50° C. to yield 4-methylbenzamidine hydrochloride (compound of Formula 16) in 90% yield.

5C. Formula A Where $R^1$ is 4-Methylphenyl; $R^2$ is Methyl; $R^3$ is Hydrogen; $R^4$ and $R^5$ are Phenyl; m is 2; n is 0; and q is 0

One mole of the product of step 5B was dissolved in 2 liters of 99% ethanol. 1.1 Moles of butanedione were added dropwise, the solution was warmed to reflux and refluxed for 20 hours. The solution was allowed to cool to 30° C. and 1 mole of powdered N-(diphenylmethyl)piperazine was added portionwise. This was followed by the addition of 1 liter of water, 1.5 equivalents of sodium hydroxide (as 12N solution), and 1.1 equivalents of lithium bromide. The solution was filtered to remove insolubles and then refluxed for 5 hours. The solution was allowed to cool to room temperature and was stirred overnight, forming the title compound as a precipitate.

The precipitate was filtered and the filter cake was added to an ethanol:water mixture (60:40) in the ratio of 3 liters of solvent mixture to 1 kilogram of filter cake. The solution was warmed to 70° C. for one hour and then allowed to cool to room temperature. The precipitate formed was filtered and dried overnight at 80° C. under vacuum to give 1-diphenylmethyl-4-[2-(-4-methylphenyl)- 5-methyl-1H-imidazol-4-yl)methyl]piperazine, the title compound, in 88% yield.

5D. TriHCl Salt of Formula A Where $R^1$ is 4-Methylphenyl; $R^2$ is Methyl; $R^3$ is Hydrogen; $R^4$ and $R^5$ are Phenyl; m is 2; n is 0; and q is 0

The trihydrochloride salt of the free base of the product of step 5C was formed by dissolving the free base of step 5C in 99% ethanol at the ratio of 1.1 liter of ethanol per mole of product. One mole of 1N HCl solution was slowly added. The solution was filtered and then warmed to 60° C. With slow addition, 250 ml of 12N HCl solution were added. The solution was slowly cooled to −10° C. and the precipitate was filtered off and dried under vacuum at 100° C. for 48 hours to yield 1-diphenylmethyl-4-[2-(-4-methylphenyl)-5-methyl-1H-imidazol- 4-yl)methyl]piperazine trichydrochloride, m.p. 204°–205° C.

5E. Formula A. Varying $R^1$

Similarly, following the procedure of parts A, B and C above, but replacing 4-methylbenzonitrile with:
  benzonitrile;
  4-chlorobenzonitrile;
  3-trifluoromethylbenzonitrile,
there is obtained:
  1-diphenylmethyl-4-[2-phenyl-5-methyl-1H-imidazol-4-yl)methyl]piperazine;
  1-diphenylmethyl-4-[2-(-4-chlorophenyl)-5-methyl-1H-imidazol- 4-yl)methyl]piperazine; and
  1-diphenylmethyl-4-[2-(-3-trifluoromethylphenyl)-5-methyl- 1H-imidazol-4-yl)methyl]piperazine.

5F. Formula A. Varying $R^2$ and $R^3$

Similarly, following the procedure of parts A, B and C above, but replacing butanedione with:
  3,4-hexanedione;
  2,3-hexanedione;
  2,3-heptanedione; and
  3,4-heptanedione,
there is obtained, respectively:
  1-diphenylmethyl-4-[1-(2-(4-methylphenyl)-5-ethyl-1H-imidazol- 4-yl)ethyl]piperazine;
a mixture of:
  1-diphenylmethyl-4-[1-(2-(4-methylphenyl)- 5-methyl-1H-imidazol-4-yl)propyl]piperazine, and
  1-diphenylmethyl-4-[(2-(4-methylphenyl)- 5-propyl-1H-imidazol-4-yl)methyl]piperazine;
a mixture of:
  1-diphenylmethyl-4-[1-(2-(4-methylphenyl)- 5-methyl-1H-imidazol-4-yl)butyl]piperazine, and
  1-diphenylmethyl-4-[(2-(4-methylphenyl)- 5-butyl-1H-imidazol-4-yl)methyl]piperazine; and a mixture of:
1-diphenylmethyl-4-[1-(2-(4-methylphenyl)- 5-propyl-1H-imidazol-4-yl)ethyl]piperazine, and
1-diphenylmethyl-4-[1-(2-(4-methylphenyl)- 5-ethyl-1H-imidazol-4-yl)propyl]piperazine.

5G. Formula A Where $R^1$ is 4-Methylphenyl; $R^2$ is Methyl; $R^3$ is Hydrogen; m is 2; n is 0; Varying q, $R^4$ and $R^5$ Similarly, following t he procedure of parts A, B and C above, but replacing N-(diphenylmethyl)piperazine with:
N-[di-(2-methylphenyl)methyl]piperazine;
N-[di-(3-methylphenyl)methyl]piperazine;
N-[di-(4-methylphenyl)methyl]piperazine;
N-[di-(2-t-butylphenyl)methyl]piperazine;
N-[di-(3-t-butylphenyl)methyl]piperazine;
N-[di-(4-t-butylphenyl)methyl]piperazine;
N-[di-(2-methoxyphenyl)methyl]piperazine;
N-[di-(3-methoxyphenyl)methyl]piperazine;
N-[di-(4-methoxyphenyl)methyl]piperazine;
N-[di-(2-chlorophenyl)methyl]piperazine;
N-[di-(3-chlorophenyl)methyl]piperazine;
N-[di-(4-chlorophenyl)methyl]piperazine;
N-[di-(4-fluorophenyl)methyl]piperazine;
N-benzylpiperazine;
N-[1-(4-chlorophenyl)-1-(phenyl)methyl]piperazine;
N-(2,2-diphenylethyl)piperazine;
N-[3-(Phenyl)-3-(4-methoxyphenyl)propyl]piperazine; and
N-(4 ,4-diphenylbutyl)piperazine,
there is obtained:
1-[di-(2-methylphenyl)methyl]-4-[(2-(4-methylphenyl)-5-methyl-1H-imidazol-4-yl)methyl]piperazine;
1-[di-(3-methylphenyl)methyl] -4-[(2-(4-methylphenyl)-5-methyl-1H-imidazol-4-yl) methyl]piperazine;
1-[di-(4-methylphenyl)methyl] -4-[(2-(4-methylphenyl)-5-methyl-1H-imidazol-4-yl)methyl]piperazine;
1-[di-(2-t-butylphenyl)methyl]-4-[(2- (4-methylphenyl)-5-methyl-1H-imidazol-4-yl)]piperazine;
1-[ di-(3-t-butylphenyl)methyl]-4-[ (2-(4-methylphenyl)-5-methyl-1H-imidazol-4-yl) methyl]piperazine;
1-[di-(4-t-butylphenyl)methyl]-4-[(2-(4-methylphenyl)-5-methyl-1H-imidazol-4-yl)methyl]piperazine;
1-[di-(2-methoxyphenyl)methyl]-4-[(2-(4-methylphenyl)- 5-methyl-1H-imidazol-4-yl)methyl]piperazine;
1-[di-(3-methoxyphenyl)methyl]-4-[(2-(4-methylphenyl)- 5-methyl-1H-imidazol-4-yl)methyl]piperazine;
1-[di-(4-methoxyphenyl)methyl]-4-[(2-(4-methylphenyl)- 5-methyl-1H-imidazol-4-yl)methyl]piperazine;
1-[di-(2-chlorophenyl)methyl]-4-[ (2-(4-methylphenyl)-5-methyl-1H-imidazol-yl)methyl] piperazine;
1-[di-(3-chlorophenyl)methyl]-4-[ (2-(4-methylphenyl)-5-methyl-1H-imidazol-4-yl)methyl]piperazine;
1-[ di-(4-chlorophenyl)methyl]-4-[ (2-(4-methylphenyl)-5-methyl-1H-imidazol-4-yl)methyl] piperazine, the trihydrochloride salt of which has a melting point of about 225° C.;
1-[di-(4-fluorophenyl)methyl]-4-[(2-(4-methylphenyl)-5-methyl-1H-imidazol-4-yl)methyl]piperazine, the trihydrochloride salt of which has a melting point of about 210° C.;
1-benzyl-4-[(2-(4-methylphenyl)-5-methyl-1H-imidazol-4-yl)methyl]piperazine;
1-[1-(4-chlorophenyl)-1-(phenyl)methyl]-4-[(2-(4-methylphenyl)- 5-methyl-1H-imidazol-4-yl)methyl]piperazine;
1-(2,2-diphenylethyl)-4-[(2-(4-methylphenyl)- 5-methyl-1H-imidazol-4-yl)methyl]piperazine;
1-[3-(phenyl)-3-(4-methyoxyphenyl)propyl]-4-[(2-(4-methylphenyl)- 5-methyl-1H-imidazol-4-yl)methyl]piperazine; and
1-(4,4-diphenylbutyl)-4-[(2-(4-methylphenyl)- 5-methyl-1H-imidazol-4-yl)methyl]piperazine.

5H. Formula A Varying m

Similarly, by following the procedures of Parts A–G above, but replacing the piperazines there-used with the corresponding diazepines, the compounds of Formula A wherein m is 3 are obtained.

EXAMPLE 6

Conversion of Free Compound To Salt

Trihydrochloride salt—The hydrochloride salt was obtained by addition of hydrochloric acid to the free base of a compound of Formula A dissolved in ethanol or ether. See step D of Example 5.

Monohydrochloride salt—100 g. of 1-diphenylmethyl-4-[2-(-4-methylphenyl)-5-methyl-1H-imidazol- 4-yl)methyl] piperazine were dissolved in 300 ml of ethanol at 95° C. To this solution 1 equivalent of 1N HCl was added with stirring. The reaction mixture was stirred at room temperature for 2 hours then the solvents were evaporated off under reduced pressure. The residue was dissolved in ether and the precipitate was filtered. The precipitate was recrystallized from isopropyl ether:acetone (1:1) to yield 1-diphenylmethyl-4-[ 2-(-4-methylphenyl)-5-methyl-1H-imidazol-4-yl)-methyl] piperazine monohydrochloride, m.p. 186°–188° C. with decomposition.

Monomaleate salt—5 g. (0.0115 mole) of 1-diphenylmethyl-4-[2-(-4-methylphenyl)-5-methyl- 1H-imidazol-4-yl)-methyl]piperazine were dissolved in 300 ml of ethanol at 95° C. To this solution 1.34 g (0.0115 mole) of maleic acid was added with stirring. The reaction mixture was stirred at room temperature for 2 hours then the solvents were evaporated off under reduced pressure. The residue was dissolved in ether and the precipitate was filtered. The precipitate was recrystallized from isopropyl ether:acetone (1:1) to yield 1-diphenylmethyl-4-[2-(-4-methylphenyl)-5-methyl-1H-imidazol-4-yl)-methyl]piperazine monomaleate, m.p. 164°–166° C. with decomposition.

Trifumarate salt—To 5 g. of 1-diphenylmethyl-4-[ 2-(-4-methylphenyl)-5-methyl-1H-imidazol-4-yl)methyl] piperazine (0.0115 mole) in acetone (100 ml) there was added 1.33 g. (0.0115 mole) of fumaric acid. The solution was heated to reflux, allowed to cool to room temperature, and allowed to stand at room temperature until precipitate formed. The precipitate was collected by filtration and recrystallized from ethanol to give the fumarate salt of 1-diphenylmethyl-4-[2-(-4-methylphenyl)- 5-methyl-1H-imidazol-4-yl)methyl]piperazine, m.p. 195° C. in almost quantitative yield.

In a similar manner, all compounds of Formula A in free base form can be converted to the acid addition salts by treatment with the appropriate acid, for example, hydrobromic acid, sulfuric acid, nitric acid, phosphoric acid, acetic acid, propionic acid, glycolic acid, pyruvic acid, oxalic acid, malonic acid, succinic acid, malic acid, maleic acid, tartaric acid, citric acid, lactic acid, benzoic acid, cinnamic acid, mandelic acid, methanesulfonic acid, ethanesulfonic acid, p-toluene- sulfonic acid, and the like.

EXAMPLE 7

Conversion of Salt to Free Base 20 g. of 1-diphenylmethyl-4-[2-(-4-methylphenyl)- 5-methyl-1H-imidazol-4-yl)methyl]piperazine trihydrochloride were solubilized in 200 ml of water. Sodium hydroxide (5N)

was added dropwise with stirring until pH 8–9. The aqueous medium was extracted twice by 200 ml of dichloromethane. The organic phases were combined then washed with cold water until neutrality. Sodium sulfate was added to dry the organic phase, then the solvent was evaporated under reduced pressure. The resulting residue was crystallized from aqueous ethanol (90%) to give 1-diphenylmethyl-4-[2-(-4-methylphenyl)- 5-methyl-1H-imidazol-4-yl)methyl]piperazine.

If desired, the extraction phase can be eliminated to allow direct recovery of the product followed by recrystallization.

EXAMPLE 8

Conversion of one Salt to Another Salt 5 g of 1-diphenylmethyl-4-[2-(-4-methylphenyl)- 5-methyl-1H-imidazol-4-yl)methyl]piperazine monofumarate were dissolved in 100 ml of hot ethanol. 3 ml of commercial concentrated HCl solution (10N) were added with stirring. The solution was refluxed for 30 minutes then the solution was allowed to cool to room temperature. The solvent was evaporated off and the residue was crystallized twice from ethanol at 98° C. to yield 1-diphenylmethyl-4-[2-(-4-methylphenyl)- 5-methyl-1H-imidazol-4-yl)methyl]piperazine trihydrochloride, m.p. 202°–204° with decomposition.

EXAMPLE 9

| Ingredients | Amounts |
|---|---|
| I.V. Formulation | |
| Active Agent | 6.0 mg/ml |
| Tartaric Acid | 6.19 mg/ml |
| Sorbitol | 40.5 mg/ml |
| Water | q.s. to 1 ml |

The acid is added to a vessel and dissolved in water, followed by the addition of the active agent, sorbitol, and water sufficient to bring the total volume to 1 ml. The resulting solution can be administered as prepared, or can be dispersed in an infusionfluid.

The active compound in the above formulation is 1-diphenylmethyl-4-[(2-(4-methylphenyl)-5-methyl-1H-imidazol-4-yl)methyl]piperazine. Other compounds of Formula A and the pharmaceutically acceptable salts thereof may be substituted therein.

EXAMPLES 10–15

The following examples illustrate the preparation of representative pharmaceutical formulations containing an active compound of Formula A, e.g., 1-diphenylmethyl-4-[(2-(4-methylphenyl)-5-methyl-1H-imidazol-4-yl)methyl] piperazine trihydrochloride. Other compounds and salts of Formula A, such as those prepared in accordance with Examples 1–8, can be used as the active compound in the formulations of Examples 10–14.

| Ingredients | Quantity per tablet, mgs. |
|---|---|
| Active compound | 25 |
| cornstarch | 20 |
| lactose, spray-dried | 153 |
| magnesium stearate | 2 |

The above ingredients are thoroughly mixed and pressed into single scored tablets.

EXAMPLE 11

| Ingredients | Quantity per capsule, mgs. |
|---|---|
| Active compound | 100 |
| lactose, spray-dried | 148 |
| magnesium stearate | 2 |

The above ingredients are mixed and introduced into a hard-shell gelatin capsule.

EXAMPLE 12

| Ingredients | Quantity per tablet, mgs. |
|---|---|
| Active compound | 1 |
| cornstarch | 50 |
| lactose | 145 |
| magnesium stearate | 5 |

The above ingredients are mixed intimately and pressed into single scored tablets.

EXAMPLE 13

| Ingredients | Quantity per capsule, mgs. |
|---|---|
| Active compound | 150 |
| lactose | 92 |

The above ingredients are mixed and introduced into a hard-shell gelatin capsule.

EXAMPLE 14

An oral suspension is prepared having the following composition:

| Ingredients | |
|---|---|
| Active compound | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s to 100 ml |

EXAMPLE 15

Ischemia (Stroke, Epilepsy)

A. Five minute model of bilateral common carotid artery occlusion in the gerbil with 72 hour survival 1) Normal animals—Using the procedure of Kirino *Brain Res.*, 239, 57 (1982), microscopic sections (8 mm) of brain tissue were obtained and stained with cresyl fast violet and haematoxylin-eosin. Abnormal brain cells were counted and expressed as a percentage of the total area counted using the procedure of Alps, et al, *Br. J. Pharmacol.* Proc. Suppl., 88, 250P (1986). The findings for 10 animals with 100 microscopic fields counted were: mean % abnormal neurones= 4.54±0.44%.

2) Sham-operated animals—The animals were anesthetized with a halothane-nitrous oxide-oxygen mixture. (Halothane was initially 5% then reduced to 1.5%. The gases were delivered via face mask.) Carotid arteries were surgically exposed (no ischemia) and survival time was 72 hours post-surgery, The microscopic sections were prepared and counted as in 1) above. In this case 7 animals were used and 100 microscopic fields were counted. The results were: mean % abnormal neurones=4.61±0.31%.

3) Untreated ischemic controls—In this case animals were subjected to 5 minute bilateral carotid artery occlusion with 72 hour survival. The microscopic sections were prepared and counted as in 1) above. In this case 12 animals were used and 120 microscopic fields were counted. The results were: mean % abnormal neurones= 78.30±2.94%.

4) Parenteral, 15 minute pre-ischemia treated—The animals were given 500 mg/kg i.p. of 1-diphenylmethyl-4-[(2-(4-methylphenyl)-5-methylimidazol-4-yl)methyl]piperazine trihydrochloride 15 minutes prior to ischaemic insult. The treatment was repeated b.i.d. for 72 hours. The microscopic sections were prepared and counted as in 1) above. In this case 10 animals were used and 100 microscopic fields were counted. The results were: mean % abnormal neurones= 26.90±3.30%.

5) Parenteral 15 minute pre-ischemia treated—The animals were given 250 mg/kg i.p. of 1-diphenylmethyl-4-[(2-(4-methylphenyl)-5-methylimidazol-4-yl)methyl-] piperazine trihydrochloride 15 minutes prior to ischaemic insult. Treatment was repeated b.i.d. for 72 hours. The microscopic sections were prepared and counted as in 1) above. In this case 6 animals were used and 60 microscopic fields were counted. The results were: mean % abnormal neurones= 27.20±4.30%.

6) Parenteral 15 minute post-ischemia treated—The animals were given 500 mg/kg i.p. of 1-diphenylmethyl- 4-[(2-(4-methylphenyl)-5-methylimidazol-4-yl)methyl-] piperazine trihydrochloride 15 minutes after ischaemic insult. The treatment was repeated b.i.d. for 72 hours. The microscopic sections were prepared and counted as in 1) above. In this case 9 animals were used and 90 microscopic fields were counted. The results were: mean % abnormal neurones= 41.70±4.60%.

7) Oral, pre-ischemia treated—The animals were given 5 mg/kg p.o. b.i.d. of 1-diphenyl-methyl-4-[(2-( 4-methylphenyl)-5-methylimidazol-4-yl)-methyl]piperazine trihydrochloride for 3 days and on the 4th day at 1 hour pre-ischaemic. Treatment was repeated b.i.d. for 72 hours. The microscopic sections were prepared and counted as in 1) above. In this case 11 animals were used and 110 microscopic fields were counted. The results were: mean % abnormal neurones= 3.00±1.00%.

8) Oral, pre-ischemia treated—The animals were given 10 mg/kg p.o. of 1-diphenyl-methyl-4-[(2-( 4-methylphenyl)-5-methylimidazol-4-yl)-methyl]piperazine trihydrochloride for 3 days and on 4th day at 1 hour pre-ischaemia. Treatment was repeated b.i.d. for 72 hours. The microscopic sections were prepared and counted as in 1) above. In this case 9 animals were used and 90 microscopic fields were counted. The results were: mean % abnormal neurones= 22.00±3.10%.

B. Ten minute Model of four vessel occlusion with 72 hour survival.

The procedure used was that of Alps, et al., Neurology, 37, 809 (1987). The object of this assay was to count abnormally appearing cells in 7 different areas and exymers as a percentage of the total area counted. The number of counts per structure depended upon size, e.g., cortical areas had double the number of other areas. Mean whole brain scores were also determined for percent abnormalities. Normal brains were also used to account for incidence of artifact changes attributed to the fixation process.

1) Normal animals—Under pentobarbital anesthesia samples were obtained, fixed with 10% buffered formal gab and microscopic samples were prepared as described in A above. In this case 6 animals were used with the results shown in the below table.

| Brain Area | Mean % Abnormal Neurones | No. Fields Counted |
|---|---|---|
| Hip $CA_1$ | 1.45 ± 0.40% | 60 |
| Hip $CA_{2-5}$ | 0.43 ± 0.20% | 60 |
| Hip Cortex | 2.90 ± 0.64% | 120 |
| Striatum | 5.80 ± 0.54% | 60 |
| Str. Cortex | 3.22 ± 0.70% | 120 |
| Thalmus | 4.38 ± 0.92% | 60 |
| Purk. cells | 5.61 ± 1.88% | 60 |
| Mean Brain score | 3.33 ± 0.33% | 540 |
| mean score per area | 3.39 ± 0.76% | 7 |

2) Untreated (saline) ischemic controls—The animals were subjected to 10 minutes of bilateral common carotid artery occlusion (with previously surgically sealed vertebral arteries) with 72 hours survival. The microscopic sections were prepared as in 1) above. In this case 11 animals were used with the results shown in the below table.

| Brain Area | Mean % Abnormal Neurones | No. Fields Counted |
|---|---|---|
| Hip $CA_1$ | 71.60 ± 3.00% | 110 |
| Hip $CA_{2-5}$ | 23.80 ± 2.70% | 110 |
| Hip Cortex | 48.50 ± 2.20% | 220 |
| Striatum | 45.10 ± 2.60% | 110 |
| Str. Cortex | 42.50 ± 2.10% | 220 |
| Thalamus | 35.30 ± 2.00% | 110 |
| Purk. cells | 32.10 ± 3.40% | 110 |
| Mean score per area | 42.70 ± 5.80% | 7 |

Parenteral, post-ischaemia treated—The animals were given 100 mg/kg i.a. of 1-diphenyl-methyl-4-[(2-( 4-methylphenyl)-5-methylimidazol-4-yl)-methyl]piperazine trihydrochloride 5 minutes post-ischaemia plus 500 mg/kg i.p. of 1-diphenyl-methyl-4-[(2-(4-methylphenyl)-5-methylimidazol- 4-yl)-methyl]piperazine trihydrochloride 15 minutes post-ischaemia. The microscopic sections were prepared according to 1) above. In this case 5 animals were used with the results shown in the below table.

| Brain Area | Mean % Abnormal Neurones | No. Fields Counted |
|---|---|---|
| Hip $CA_1$ | 16.76 ± 4.00% | 50 |
| Hip $CA_{2-5}$ | 1.78 ± 0.99% | 50 |
| Hip Cortex | 2.41 ± 0.30% | 100 |
| Striatum | 1.54 ± 0.33% | 50 |
| Str. Cortex | 2.01 ± 0.29% | 100 |
| Thalamus | 0.64 ± 0.25% | 50 |
| Purk. cells | 2.22 ± 0.79% | 50 |

C. The effect of 1-diphenyl-methyl-4-[(2-( 4-methylphenyl)-5-methylimidazol-4-yl)-methyl]piperazine trihydrochloride on pentylenetetrazole-induced seizures and mortality in the mouse.

The procedure used was that described in Allely, and Alps, *Br. J. Phramacol.* Proc. Suppl., 92, 605P (1987). Groups of 20 or more (see n in table) male CDI mice were predosed with 500 mg/kg i.p. of 1-diphenyl-methyl-4-[ (2-(4-methylphenyl)-5-methylimidazol-4-yl)methyl]piperazine trihydrochloride at one of three dosing schedules—A (15 minutes), B (60 minutes), or C (3 days b.i.d. plus 15 minutes on 4th day)—before challenging with 100 mg/kg of pentylenetetrazole s.c. The animals were then observed for a 30 minute period and the occurrence of clonic or tonic seizures or death noted. Statistical analysis was by a Chi squared test of association. Results compared against saline treated animals are shown in the below table.

| Predose Schedule | Predosed mg/kg i.p. | n | % clonic seizures | % tonic seizures | % death |
|---|---|---|---|---|---|
| Saline | | | | | |
| — | — | 40 | 92.5 | 80.0 | 70.0 |
| Drug | | | | | |
| A | 500 | 20 | 85.0 | 85.0 | .50.0 |
| B | 500 | 25 | 88.0 | 64.0 | 36.0 |
| C | 500 | 24 | 66.7 | 41.7 | 45.0 |

In an oral dose ranging study in rats of 1-diphenyl-methyl-4-[ (2-(4-methylphenyl)-5-methylimidazol- 4-yl)methyl]piperazine trihydrochloride no death or clinical signs of toxicity were seen at up to 25 mg/kg/day.

EXAMPLE 16

Diuresis

Male normotensive rats weighing 290–380 g were divided into four groups of seven animals. All animals were fasted and deprived of water overnight. The following morning, each group of rats was hydrated with deionized water (20 mg/kg. p.o.) 45 minutes prior to the administration of vehicle (1% polysorbate 80 in deionized water) or 1-diphenyl-methyl-4-[(2-(4-methylphenyl)-5-methylimidazol- 4-yl)methyl]piperazine trihydrochloride at doses of 5, 15, or 30 mg/kg p.o. Fifteen minutes post-drug, the animals were saline loaded (30 ml/kg, p.o. 0.9% sodium chloride) and placed individually in metabolism cages. Urine was collected at 1, 3, and 6 hour intervals post-dose. Urine volumes were measured and sodium and potassium levels were determined by flame photometry. Differences between control and treated values were evaluated by one way analysis of variance. 1-diphenyl-methyl-4-[(2-(4-methylphenyl)-5-methylimidazol- 4-yl)methyl]piperazine trihydrochloride (30 mg/kg, p.o.) produced significant ($p < 0.05$) diuresis which was observed at 1 hour and 6 hours post-drug. The compound (30 mg/kg, p.o.) elicited a significant natriuretic effect at the 3 and 6 hour time periods. No significant kaliuretic effects were observed following compound administration.

| Cumulative time | control vehicle* | 5 mg/kg p.o. | 15 mg/kg p.o. | 30 mg/kg p.o. |
|---|---|---|---|---|
| | | Urine Volume (ml) | | |
| 1 hour | 3.3 ± 2.7 | 5.7 ± 2.5 | 5.7 ± 4.4 | 6.5 ± 2.3 |
| 3 hours | 7.3 ± 3.3 | 9.5 ± 3.6 | 9.8 ± 3.2 | 10.5 ± 2.5 |
| 6 hours | 9.6 ± 3.9 | 11.8 ± 3.9 | 11.7 ± 3.3 | 14.6 ± 1.4 |

| Cumulative time | control vehicle* | 5 mg/kg p.o. | 15 mg/kg p.o. | 30 mg/kg p.o. |
|---|---|---|---|---|
| | | Sodium ion (mEq) | | |
| 1 hour | .06 ± .08 | .07 ± .06 | .12 ± .16 | .15 ± .12 |
| 3 hours | .28 ± .31 | .39 ± .25 | .44 ± .20 | .79 ± .38 |
| 6 hours | .55 ± .44 | .73 ± .32 | .68 ± .28 | 1.48 ± .24 |
| | | Potassium ion (mEq) | | |
| 1 hour | .03 ± .03 | .04 ± .03 | .04 ± .05 | .04 ± .03 |
| 3 hours | .13 ± .09 | .16 ± .09 | .12 ± .06 | .15 ± .08 |
| 6 hours | .22 ± .12 | .26 ± .12 | .20 ± .08 | .27 ± .06 |

EXAMPLE 17

Irritable Bowel Syndrome

The test used is a modification of the method of Macht and Barba-Gose, *J. Amer. Pharm. Assoc.*, 20, 558 (1931), which traces the transit of a charcoal meal through the intestine as an index of transit time. In the present model, intestinal transit in conscious mice (15–20 g) was accelerated with an oral dose of barium chloride (300 mg/kg) administered at the same time as the charcoal meal. The animals were sacrificed 10 minutes later and the distance travelled by the charcoal measured. 1-diphenyl-methyl-4-[(2-(4-methylphenyl)-5-methylimidazol- 4-yl)methyl]piperazine trihydrochloride was given as a 15 minute oral pre-treatment and its effect on non-stimulated or barium-stimulated intestinal transit of the charcoal meal was calculated. The results were expressed as inhibition percentage of the total transit induced by $Ba^{+2}$, and not as the inhibition percentage of the portion representing the $Ba^{+2}$ effect and are shown in the below table.

| Dose 15 min mg/kg p.o. | % Change $Ba^{+2}$ | % Inhibition of $Ba^{+2}$ effect | % Inhibition Normal Transit |
|---|---|---|---|
| 5 | +93% | +14% | −19.3% |
| 25 | +93% | −30.4% | −28.7% |
| 60 | +93% | −31.7% | −16.1% |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the structure represented by the formula:

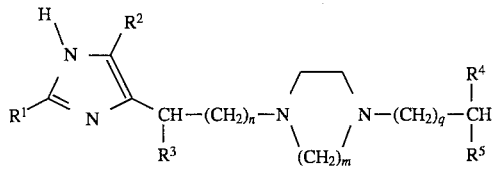

wherein:

$R^1$ is aryl, lower alkyl, cycloalkyl or hydrogen;

$R^2$ is aryl, lower alkyl or hydrogen;

$R^3$ is lower alkyl, hydroxy, or hydrogen;

$R^4$ is aryl or hydrogen;

$R^5$ is aryl or hydrogen;

m is two or three;

n is zero; and q is zero, one, two, or three;

or a pharmaceutically acceptable salt thereof, having a detectable amount of a lithium compound used or produced in the process of its manufacture.

2. The compound of claim 1 wherein $R^2$ is lower alkyl and $R^3$ is lower alkyl having one carbon atom less than $R^2$, or $R^3$ is hydrogen when $R^2$ is methyl.

3. The compound of claim 1 wherein the lithium compound is lithium bromide or lithium hydroxide.

4. The compound of claim 2 wherein the lithium compound is lithium bromide or lithium hydroxide.

5. The compound of claim 4, wherein said compound is 1-(diphenylmethyl)-4-[ (2-(4-methylphenyl)-5-methyl-1H-imidazol- 4-yl)methyl]piperazine.

6. The compound of claim 1, wherein said compound is 1-(diphenylmethyl)-4-[ (2-(4-methylphenyl)-5-methyl-1H-imidazol- 4-yl)methyl]piperazine.

7. A pharmaceutically acceptable salt of the compound 1-(diphenylmethyl)-4-[ (2-(4-methylphenyl)-5-methyl-1H-imidazol-4-yl)methyl]piperazine.

8. The pharmaceutically acceptable salt of claim 7, wherein said salt is the tartrate.

9. The pharmaceutically acceptable salt of claim 7, wherein said salt is the citrate.

10. The pharmaceutically acceptable salt of claim 7, which is the acid addition salt of tartaric acid, citric acid and said compound.

* * * * *